United States Patent
Scolastico et al.

(10) Patent No.: US 6,235,877 B1
(45) Date of Patent: May 22, 2001

(54) PEPTIDO-MIMETIC COMPOUNDS CONTAINING RGD SEQUENCE USEFUL AS INTEGRIN INHIBITORS

(75) Inventors: Carlo Scolastico, Milan; Giuseppe Giannini, Pomezia, both of (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/366,198

(22) Filed: Aug. 4, 1999

(51) Int. Cl.$^7$ ....................................................... C07K 5/10
(52) U.S. Cl. ......................... 530/330; 530/331; 530/317; 514/9; 514/18
(58) Field of Search ..................... 530/330, 331, 530/317; 514/18, 9

(56) References Cited

U.S. PATENT DOCUMENTS

| | | | |
|---|---|---|---|
| 5,766,591 | 6/1998 | Brooks et al. | 424/184.1 |
| 5,767,071 | 6/1998 | Palladino et al. | 514/11 |
| 5,773,412 | 6/1998 | Cheng et al. | 514/11 |

FOREIGN PATENT DOCUMENTS

| | | |
|---|---|---|
| WO 91/15515 | 10/1991 | (WO) . |
| WO 92/17492 | 10/1992 | (WO) . |
| WO 94/29349 | 12/1994 | (WO) . |
| WO 95/00544 | 1/1995 | (WO) . |
| WO 97/06791 | 2/1997 | (WO) . |
| WO 97/08203 | 3/1997 | (WO) . |
| WO 98/56407 | 12/1998 | (WO) . |
| WO 98/56408 | 12/1998 | (WO) . |

OTHER PUBLICATIONS

Abstract of Dechantsreiter (J. Med. Chem. 42, 3033), 1999.*
Abstract of Haubner (J. Nucl. Med 40, 1061), 1999.*
Abstract of Kang (Cancer Research 59, 3754), 1999.*
Belvisi et al XXV Convegno Nazionale Div. di Chimica Organica Societa Chimica ItalianaSep./ 1998 Analisi Conformazionale Di Peptidi Contenenti Unita Reverse–Turn Mimetiche.
Haubner et al J. Am. Chem. Soc. 1996, 118, 7881–7891 Cyclic RGD Peptides Containing β–Turn Mimetics.
Gennari et al Eur. J. Org. Chem. 1999, 379–388 Solid–Phase Synthesis of Peptides Containing Reverse–A Turn Mimetic Bicyclic Lactams.
Belvisi et al Eur. J. Org. Chem. 1999, 389–400 Conformational Preferences of Peptides Containing Reverse–Turn Mimetic Bicyclic Lactams: Inverse γ–Turns versus Type–II' β–Turns—Insights into β–Hairpin Stability.

* cited by examiner

Primary Examiner—Christopher S. F. Low
Assistant Examiner—David Lukton
(74) Attorney, Agent, or Firm—Nixon & Vanderhye

(57) ABSTRACT

The present invention discloses compounds of formula (I)

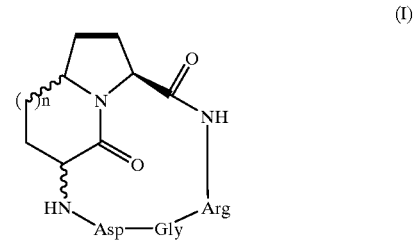

(I)

wherein n is the number 0, 1 or 2. There are also disclosed processes for the preparation of said compounds, together with methods for treating pathologies related to an altered $\alpha_v\beta_3$ integrin-mediated cell attachment, in particular wherein the inhibition of angiogenesis is desired, for example in tumors, also associated with metastasis.

13 Claims, 8 Drawing Sheets

Scheme 2. Synthesis of the 6,5-fused "cis" lactams 2a and 8a.

Scheme 3. Stereoselective hydrogenation of 27 with chiral phosphine-Rh catalyst.

Scheme 4. Synthesis of the 7,5-fused "cis" lactams 3a and 9a.

Scheme 5. Synthesis of the 5,5-fused "cis" lactams 1a and 7a.

Scheme 6. Alternative synthesis of the 5,5-fused "cis" lactams 1a and 7a.

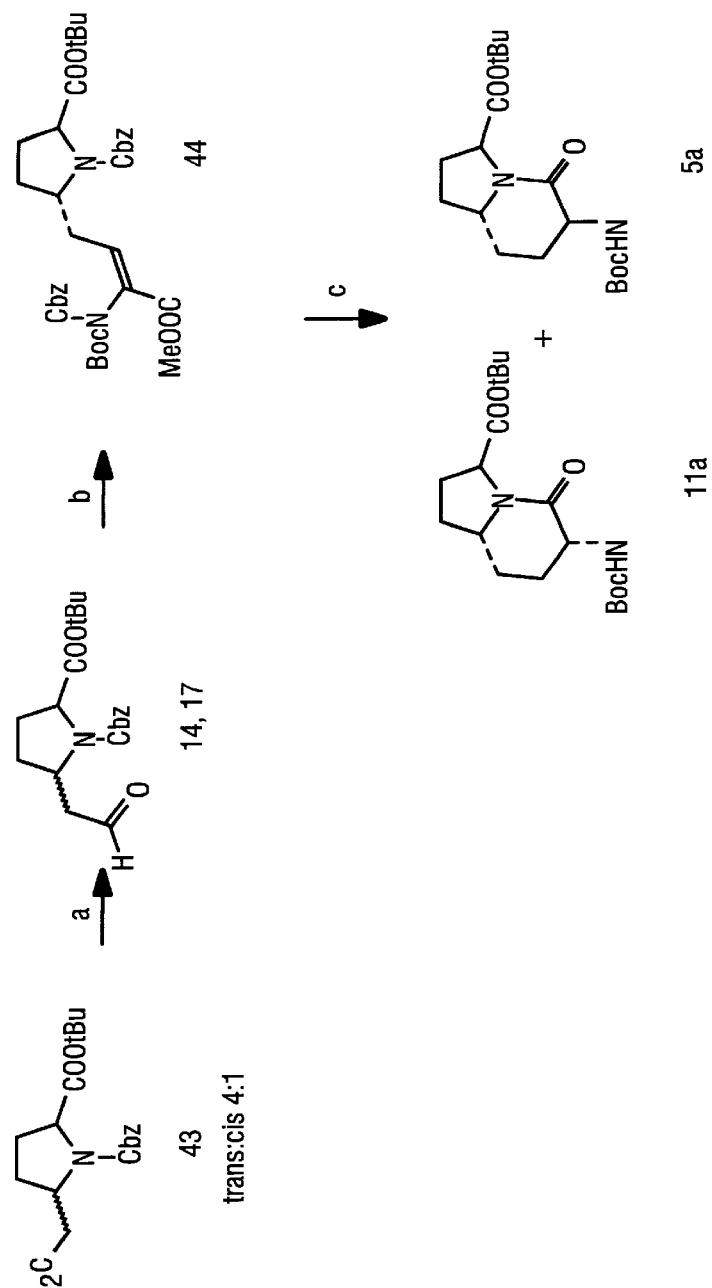
Scheme 7. Synthesis of the 6,5-fused "trans" lactams 5a and 11a.

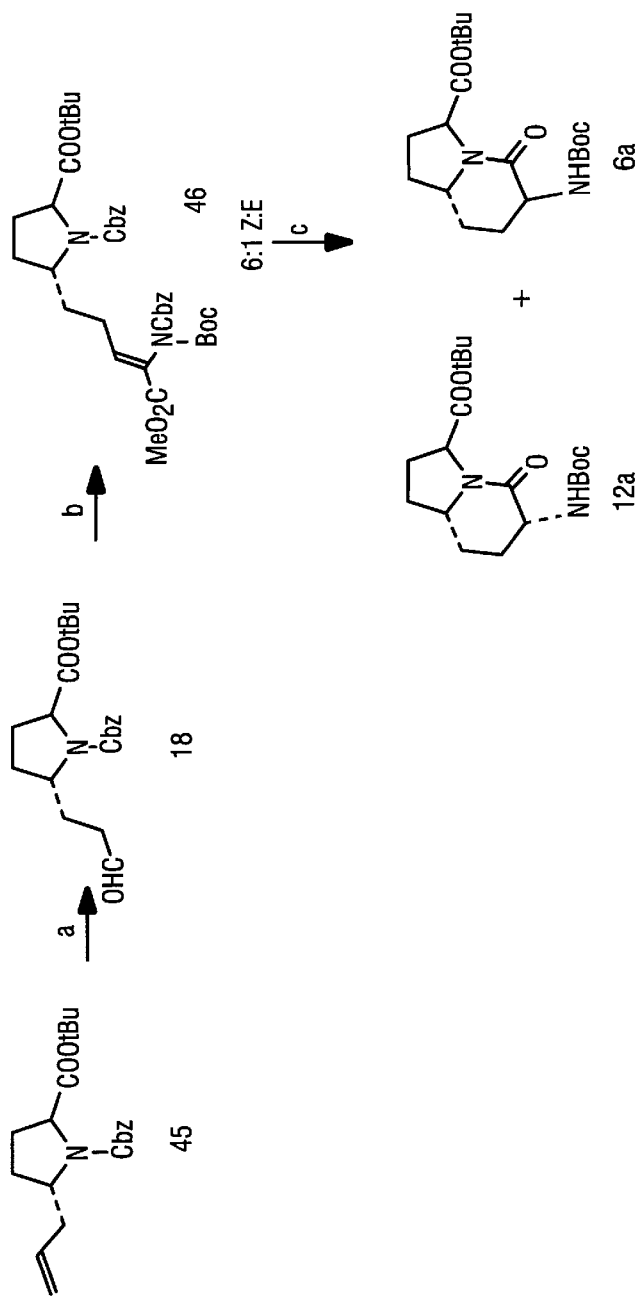
Scheme 8. Synthesis of the 7,5-fused "trans" lactams 6a and 12a.

PEPTIDO-MIMETIC COMPOUNDS CONTAINING RGD SEQUENCE USEFUL AS INTEGRIN INHIBITORS

The present invention relates to cyclic peptidomimetic compounds, in particular to cyclic peptidomimetic compounds having azabicycloalkane structure and containing the RGD (Arg-Gly-Asp) sequence. Said compounds have inhibiting action on $\alpha_v\beta_3$-receptor of the integrin family. The compounds of the present invention are endowed with antiangiogenic properties, hence are useful as medicaments, preferably for the treatment of tumors.

BACKGROUND OF THE INVENTION

The first molecule with antiangiogenic activity was discovered in 1975 by Henry Brem and Judah Folkman in cartilaginous tissues.

In the 80s it was found that interferon ($\alpha/\beta$) is effective in inhibiting tumor angiogenesis.

In 1998, it was widely published, also in the media, that angiostatin and endostatin discovered by J. Folkman at Harvard Medicinal School and Boston Children's Hospital were giving very encouraging results in tumor treatment.

To-date, about 30 molecules are tested in clinical trials (Phase I–III).

Of these 30 molecules, only two drugs, of which one is an antibody, are in clinical trials for their activity in inhibiting endothelial specific integrins.

It is calculated that only in the USA, about 9 million patients could benefit from an antiangiogenic therapy.

Recently, FDA has approved clinical trials for the combination of IL-10 with Thalidomide and Methoxyestradiol.

Angiogenesis is intended as the formation of new capillary blood vessels. This natural phenomenon is involved both in physiological processes, as reproduction, and in pathological occurrences, as wound healing, arthritis and tumor vascularization.

A number of growth factors have been identified as capable of promoting angiogenesis, through direct induction of proliferation and/or chemiotaxis of endothelial cells. Other factors, instead, act indirectly, by stimulating other cell types (mast cells, macrophages), which, on their turn, produce angiogenic factors. The presence of growth factors, such as bFGF and VEGF, near a resting capillary net, suggested that angiogenesis might be the outcome of an unbalance between pro- and anti-angiogenic factors.

In the last years, it was reported that tumor growth and metastasis formation is strictly dependent on the development of new vessels capable of vascularizing the tumor mass.

Antiangiogenic tumor therapy is strongly desired by physicians for the following reasons:

specificity: tumor neovascularization is the target;
bioavailability: the antiangiogenic agent is targeted toward endothelial cells, easily reached without the well-known problems of chemotherapy, which is directed on the tumor cell;
chemoresistance; this is the most striking advantage, in fact, endothelial cells are genetically stable and it is quite difficult to observe drug resistance;
angiogenic blockade avoids metastatic cells to diffuse through blood circulation;
apoptosis blocking angiogenesis makes tumor cell suffer from oxygen and nutrition lack, thus inducing apoptosis;
antiangiogenic therapy does not give rise to side effects typical of chemotherapy.

The endogenous pro-angiogenic factors to date known are acid/basic Fibroblast Growth factor (a/bFGF) and Vascular Endothelial Growth Factor (VEGF), and its subtype B and C, Angiogenin, Endothelial Growth Factor (EGF), Platelet derived-Endothelial Cell Growth Factor (PD-ECGF), Transforming Growth Factor-$\alpha$ (TGF-$\alpha$), Transforming Growth Factor-$\beta$ (TGF-$\beta$), Tumor Necrosis Factor-$\alpha$ (TNF-$\alpha$).

Retinoids are tested as potential antiangiogenic agents.

Some PK-C inhibitors, such as Calphostin-C, phorbol esters and Staurosporin, can block angiogenesis, either partially or totally.

Integrins are a class of receptors involved in the mechanism of cell adhesion and alterations in the function of these receptors are responsible in the occurrence of a number of pathologic manifestations, for example embryogenic development, blood coagulation, osteoporosis, acute renal failure, retinopathy, cancer, in particular metastasis. Among the molecular targets involved in angiogenesis, $\alpha v\beta 3$ integrins play an important role in adhesion, motility, growth and differentiation of endothelial cells. $\alpha v\beta 3$ integrins bind the RGD sequence (Arg-Gly-Asp), which constitutes the recognition domain of different proteins, such as laminin, fibronectin and vitronectin. The role of RGD sequence is described, for example, in Grant et al., J. Cell Physiology, 1992, Saiki et al., Jpn. J. Cancer Res. 81; 668–75. Carron et al, 1998, Cancer Res. 1; 58(9):1930–5 disclosed an RGD-containing tripeptide, named SC-68448, capable of inhibiting the binding between $\alpha v\beta 3$ integrin with vitronectin ($IC_{50}=1$ nM). Other works (Sheu et al., 1197, BBA; 1336 (3):445–54—Buckle at al., 1999, Nature 397:534–9) showed that RGD peptides can diffuse through the cell membrane and bind to the protein caspase-3, inducing apoptosis.

Therefore, RGD sequence is the basis for developing antagonists of the different integrins. To date, the reasons for which in many cases a high selectivity for certain integrins is observed is not quite clear, although a different conformation of the RGD sequence can be taken as an explanation. Recent data demonstrated that this sequence is often inserted into a type II-$\beta$-turn between two $\beta$-sheets extending from the core of the protein.

Thus the problem to provide substances having high selectivity toward integrins has not been fully satisfied yet.

There is a structural constraint to this research, namely, the RGD sequence must be kept unaltered, since it is well known that any modification to this sequence implies a loss of activity.

To find the correct structure that can block the molecule in a precise reverse-turn conformation, inducing a $\beta$-turn geometry, is very critical.

It is well known that the $\alpha v\beta 3$-receptor, a member of the integrin family, is implicated in angiogenesis and in human tumor metastasis.

Metastasis of several tumor cell lines as well as tumor-induced angiogenesis can be inhibited by antibodies or small, synthetic peptides acting as ligands for these receptors (Friedlander et al.: Science 1995, 270, 1500–1502.

In order to have an inhibiting property, all the peptides must contain the Arg-Gly-Asp (RGD) sequence. Notwithstanding this RGD sequence, a high substrate specificity is present, due to different conformations of the RGD sequence in different matrix proteins (Ruoshlati et al. Science 1987, 238, 491–497). This flexibility of particular RGD portion is an obstacle to the determination of the bioactive conformation to be used in the widespread structure-activity drug design.

A solution was provided by Haubner et al. (J. Am. Chem. Soc. 1996, 118, 7881–7891) by inserting the RGD sequence in cyclic, rigid peptide structure. Spatial screening led to the highly active first-generation peptide c(RGDfV) (cyclic Arg-Gly-Asp-D-Phe-Val; WO97/06791), which shows a βII'/γ-turn arrangement. A reduction of the flexibility is a technical goal to be achieved in order to obtain antagonists of integrins. Due to the width of the integrin family and to the number of different physiological activities of said integrins, it is highly desired to obtain active agents having highly selective inhibiting action.

A solution proposed in the art was to introduce in the peptidomimetic structure a rigid building block (turn mimetics).

Despite different tentatives and a number of structures proposed, Haubner et al. (J. Am. Chem. Soc. 1996, 118, 7881–7891), identified an RGD "spiro" structure capable of providing the desired βII'/γ-turn arrangement. Actually, four different structures are enabled in this work: an (S)-proline derivative, an (R)-proline derivative, a thiazabicyclo structure and a diaza-spiro-bicyclic structure. Non-homogeneous results were obtained. The spiro structure was the only one able to adopt a βII'/γ-turn conformation, but lacks of biological activity. The (S)-proline is very active, but less selective. The (R)-proline is active and selective. The thiazabicyclo-structure is active, but has the disadvantage to be less selective.

WO91/15515 discloses cyclic peptides, also containing the RGD sequence, useful for treating thrombosis, through the selective inhibition of the platelet aggregation receptor GPIIb/IIa.

WO92/17492 discloses cyclic peptides, also containing the RGD sequence, useful for treating thrombosis, through the selective inhibition of the platelet aggregation receptor GPIIb/IIa. These peptides contain also a positively charged nitrogen containing exocyclic moiety stably bonded to the cyclic peptide through a carbonyl. No beta-turns are contained in these structures.

WO94/29349 discloses a long peptide containing a -Cys-S-S-Cys- cyclic portion for the treatment of a venous or arterial thrombotic condition. This trifunctional peptide combines both catalytic and anion binding exosite inhibition of thrombin with GP IIb/IIIa receptor inhibition, Other peptides active in treating thrombosis are disclosed in WO95/00544.

WO97/06791 discloses the use of c(RGDfV) as selective inhibitor of $\alpha_v/\gamma_5$ and useful as inhibitor of angiogenesis.

WO97/08203 discloses circular RGD-containing peptides, which comprise the motif (/P)DD(G/L)(W/L)(W/L/M).

U.S. Pat. No. 5,767,071 and U.S. Pat. No. 5,780,426 disclose non-RGD amino acid cyclic peptides binding $\alpha_v/\gamma_3$ integrin receptor.

U.S. Pat. No. 5,766,591 discloses RGD-peptides for inhibiting $\alpha_v/\gamma_3$ receptor and useful as antiangiogenesis agents. No beta turn portions are taught.

WO98/56407 and WO98/56408 disclose fibronectin antagonists as therapeutic agents and broad-spectrum enhancers of antibiotic therapy. Said fibronectin antagonists bind to a $\alpha_5\beta_1$ integrin to the purpose to prevent intracellular invasion by microbial pathogens. Some of these inhibitors are linear or cyclic peptides containing the RGD structure or antibodies. Integrin antagonists are specifically disclosed for their selectivity against $\alpha_5\beta_1$ integrin. The best of them proved to be (S)-2-[2,4,6-trimethylphenyl)sulfonyl]amino-3-[[7benzyloxycarbonyl-8-(2-pyridinylarninomethyl)-1-oxa-2,7-diazaspiro-[4,4]-non-2-en-3-yl]carbonylamino] propionic acid.

U.S. Pat. No. 5,773,412 discloses a method for altering $\alpha_v\beta_3$ integrin receptor-mediated binding of a cell to a matrix, said cell being an endothelial or smooth muscle cell, by contacting said cell with a RGD-containing cyclic peptide. Also disclosed there is a method for inhibiting angiogenesis by using this cyclic peptide. The cyclic peptide disclosed in U.S. Pat. No. 5,773,412 contains at least 6 amino acids and the RGD sequence is flanked, on the D-side, by a first amino acid which can provide a hydrogen bond interaction with an integrin receptor (Asn, Ser or Thr) and a second amino acid, that has the characteristics of hydrophobicity or conformational constraint (Tic, i.e. 1,2,3,4-tetrahydroisoquinoline-3-carboxylic acid, Pro, Phe or Ile). A selection of these peptides are taught as useful for altering the binding of osteoclasts to a matrix such as bone or for selectively altering integrin receptor binding.

It has now been found that cyclic pseudopeptides having an RGD mimetic structure characterized by an azabicycloalkane structure are endowed with selective inhibition of $\alpha_v\beta_3$ integrin-mediated cell attachment. This activity makes them useful as therapeutical agents, in particular for treating pathologies due to an altered angiogenesis, for example tumors.

BRIEF SUMMARY OF THE INVENTION

It is an object of the present invention, compounds of formula (I)

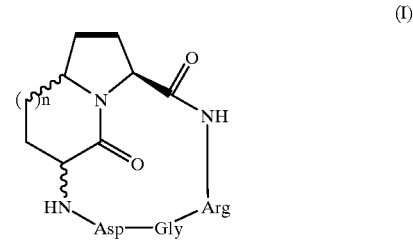

(I)

wherein n is the number 0, 1 or 2,

Asp is the amino acid L-Arginine, Gly is the amino acid Glycine and Asp is the amino acid L-Aspartic acid, and the pharmaceutically acceptable salts thereof, their racemates, single enantiomers and stereoisomers.

The compounds of formula (I) are selective inhibitors of $\alpha_v\beta_3$ receptor. Accordingly, they are useful for treating all those pathologies due to an altered $\alpha_v\beta_3$ integrin-mediated cell attachment; for example, retinopathies, acute renal failure, osteoporosis, tumors, also associated with metastasis. The compounds of the present invention can be considered as antiangiogenesis agents, in particular for the treatment of tumors, comprising tumors associated with metastasis.

Other objects of the present invention are processes for the preparation of the compounds of formula (I).

A further object of the present invention is a method for treating a subject, whether human or animal, suffering of a tumor, s by inducing an inhibition of angiogenesis, in particular for inhibiting or reducing or blocking metastatic proliferation, with the administration of a therapeutic or preventive dose of at least a compound of formula (I). Also objects of the present invention are a method for selectively inhibiting $\alpha_v\beta_3$ integrin-mediated cell attachment to an RGD-containing ligand, comprising contacting said ligand with an effective amount of a compound of formula (I); a method for treating a subject suffering from a pathology related to an altered $\alpha_v\beta_3$ integrin-mediated cell attachment comprising administering to said subject a compound of formula (I); said pathologies being for example retinopathy, acute renal failure, osteoporosis.

From the industrial application point of view, the present invention also comprises pharmaceutical compositions comprising an effective dose of at least a compound of formula (I) in admixture with pharmaceutically acceptable vehicles and/or excipients.

BRIEF DESCRIPTION OF THE DRAWINGS

The present invention shall be disclosed in detail in the foregoing also by means of examples and figures, wherein, in the figures:

FIG. 7 represents a preferred embodiment of the synthesis of 6,5-fused "trans" lactams;

FIG. 8 represents a preferred embodiment of the synthesis of 7,5-fused "trans" lactams,

DETAILED DESCRIPTION OF THE INVENTION

Figure 1:
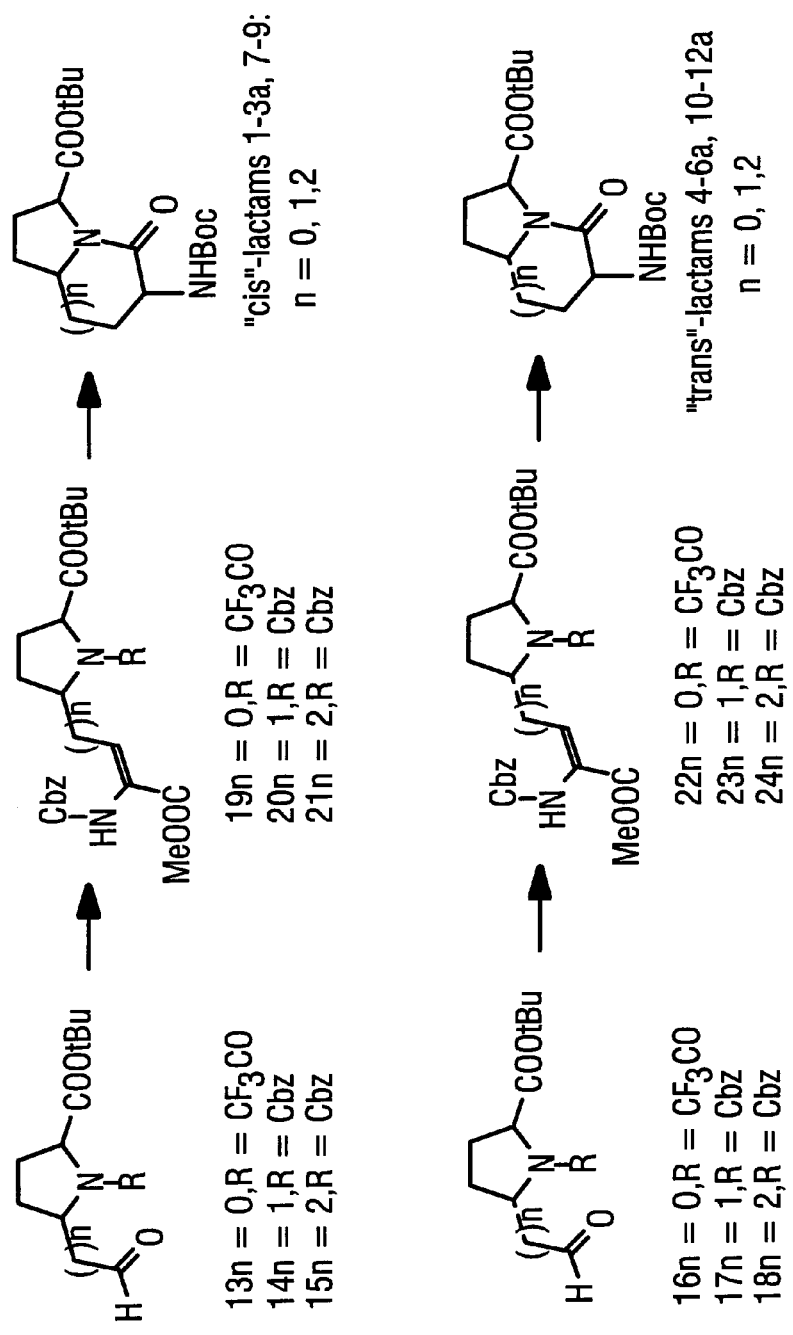
FIG. 1 represents, in an exemplary way, the general s synthesis of the lactams.

In its broadest aspects, the present invention relates to compounds of the above formula (I).

The compounds of formula (I) are peptidomimetics containing an RGD sequence. Said compounds can be seen as formed by an azabicycloalkane scaffold and an RGD sequence.

For sake of clarity, in formula (I), there is a variable part, given by the different values of n, and a fixed part, given by the RGD sequence. When n is 0, the scaffold is referred to as 5,5 azabicycloalkane, when n is 1, the scaffold is referred to as 6,5 azabicycloalkane and when n is 2, the scaffold is referred to as 7,5 azabicycloalkane The bonds written in formula (I) as a wavy line represents a stereo bond, which can be either above the plane of the page (thick bond) either below the plane of the page (thin bond). The compounds of formula (I) can exist in different stereoisomers, according to the orientation of the wavy bond. In the following table there are represented the preferred compounds of formula (I):

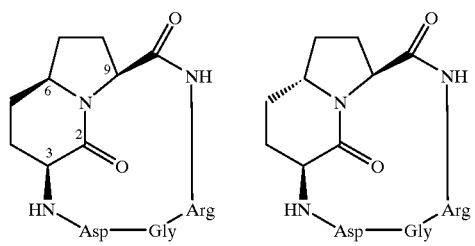

-continued

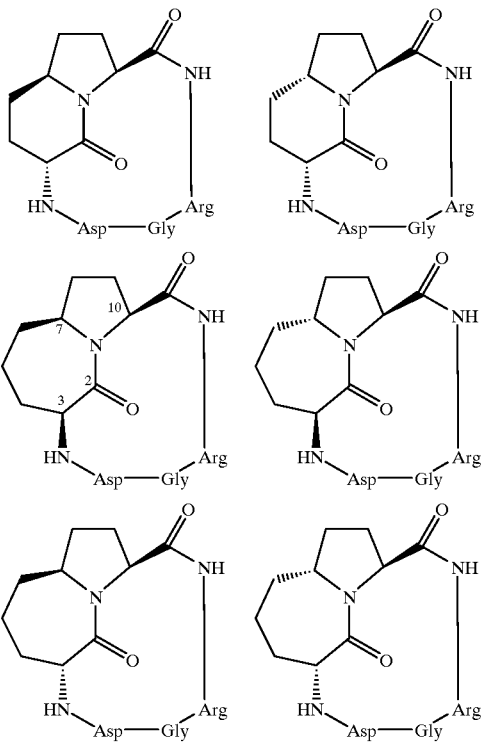

Within the boundaries of the present invention, there is disclosed a process for the preparation of the compounds of formula (I), comprising the following steps:

a) Horner-Emmons olefination of a compound of formula (II)

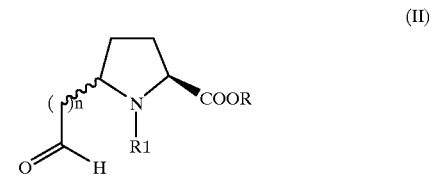

(II)

wherein
R is a lower allyl residue;
$R_1$ is a suitable nitrogen protecting group,
to give a compound of formula (III);

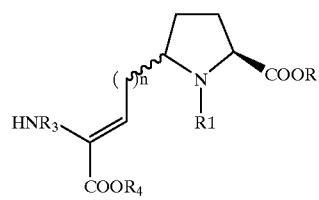

(III)

wherein $R_3$ is a suitable nitrogen protecting group, $R_4$ is a lower alkyl residue;
b) hydrogenation of said compound of formula (III) and cyclisation; and, if desired
c) separation of the stercoisorneric mixture;
d) building of the RGD cyclic sequence, and if desired
e) separation of the stereoisomeric mixture.

A process for the stereoselective synthesis of the compounds of formula (I), comprises the following steps:

a) Horner-Emmons olefination of a compound of formula (II)

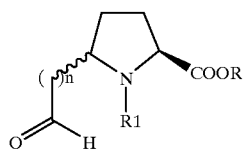

wherein

R is a lower alkyl residue;

R₁ is a suitable nitrogen protecting group, to give a compound of formula (III);

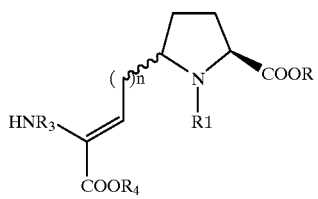

wherein R₃ is a suitable nitrogen protecting group, R₄ is a lower alkyl residue;

b) hydrogenation of said compound of formula (III) by chiral phosphine-Rh catalysed hydrogenation and cyclisation; and, if desired c) separation of the stereoisomeric mixture;

d) building of the RGD cyclic sequence and if desired e) separation of the stereoisomeric mixture.

Also disclosed are pharmaceutical composition comprising a therapeutically or preventive effective dose of at least a compound of formula (I) in admixture with pharmaceutically acceptable vehicles and/or excipients.

In its broadest aspect, the present invention advantageously teaches a method for selectively inhibiting $\alpha_v\beta_3$ integrin-mediated cell attachment to an RGD-containing ligand, comprising contacting said ligand with an effective amount of a compound of formula (I), a method for treating a subject suffering from altered angiogenesis, comprising administering to said subject a compound of formula (I), a method for the treatment of tumors in a subject comprising administering to said subject a compound of formula (I), optionally in combination with other active ingredients, in particular other antitumour agents.

The present invention shall be described in detail also by means of examples and figures, wherein, Best Mode for Carrying Out the Invention The synthesis of so-called peptidomimetics molecules has been a very active and productive field of research in drug design (J. Gante, Angew. Chem., Int. Ed. Engl. 1994, 33, 1699.—G. L. Olson, et al.: J. Med. Chem. 1993, 36, 3039.— D. C. Horwell, Bioorg.Med. Chem. Lett. 1993, 3, 797.—A. Giannis et al.: Angew. Chem., Int. Ed. Engl. 1993, 32, 1244.—B. A. Morgan: Annu. Rep. Med. Chem. 1989, 24, 243). The expectation is that these molecules will have the same biological effects as natural peptides, but at the same time, will be metabolically more stable. Of particular interest has been the replacement of reverse-turn dipeptide motifs with constrained molecules that reproduce their conformational features (ibid, M. Kahn, Ed., Peptide Secondary Structure Mimetics. Tetrahedron Symposia-in-Print No. 50 1993, 49, 3433–3689 and references therein). This goal has been frequently achieved using the azaoxobicyclo[X.Y.O] alkane skeleton and/or heteroatom analogues. This has created a demand for efficient synthetic approaches toward such molecules, and many methods have been introduced and recently reviewed (S. Hanessian et al: Tetrahedron 1997, 38, 12789–12854). One particularly effective and versatile route has been developed by Lubell et al, and employed for the preparation of enantiopure indolizidinone-type 6,5-fused bicyclic lactams (H.-G. Lombart al.: J. Org. Chem. 1996, 61, 9437–9446.—F. Polyak et al.: J. Org. Chem. 1998, 63, 5937–5949 and references therein for the syntheses of azabicycloalkane amino acids—F. Gosselin et al.: J. Org. Chem. 1998, 63, 7463–7471). Several procedures are also available for the synthesis of 7,5-fused bicyclic lactams, the majority of which require relatively long synthetic sequences. On the contrary, there is not many published protocol that allow the synthesis of 5,5-fused bicyclic lactams.

According to the present invention, the beta-turn portion of the cyclic peptide consists in an azabicycloalkane amino acid scaffold, selected from a 5,5-, 6,5- or 7,5-fused bicyclic lactams. Several 6,5- and 7,5-fused 1-aza-2-oxabicyclo [X.3.0]alkane amino acids have been synthesised, using radical (L. Colombo et al.: Tetrahedron Lett. 1995, 36, 625–628.—L. Colombo et al.: Gazz. Chim. It. 1996, 126, 543–554) or ionic reactions (L. Colombo et al. Tetrahedron 1998, 54, 5325–5336). These structures can be regarded as conformationally restricted substitutes for Ala-Pro and Phe-Pro dipeptide units, and, if their conformations meet certain criteria, they can be used to replace the central (i+1 and i+2) residues of β-turns.

The present invention provides an improved reaction sequence, amenable to large scale preparation, and allowing the synthesis of different bicyclic lactams from common intermediates, as described in the appended (FIG. 1).

Starting from 5-allyl/formyl prolines 13–18, a Z-selective Horner-Emmons olefination followed by double bond reduction has been used to build the second ring. The starting aldehydes have been stereoselectively synthesised by modifications of known procedures (vide infra). Stereo-random double bond reduction can be performed using H₂/Pd to yield, after cyclisation, mixtures of easily separable epimers. Stereoselective hydrogenation is studied for the synthesis of 6,5-fused lactams, and achieved with d.e. 80% using Rh-chiral phosphine catalysts. Structural diversity, in terms of ring size and stereochemistry of the azabicycloalkane fragment, is provided by the new strategy, and access to the less common 5,5-fused bicyclic scaffold is also secured.

Figure 2:
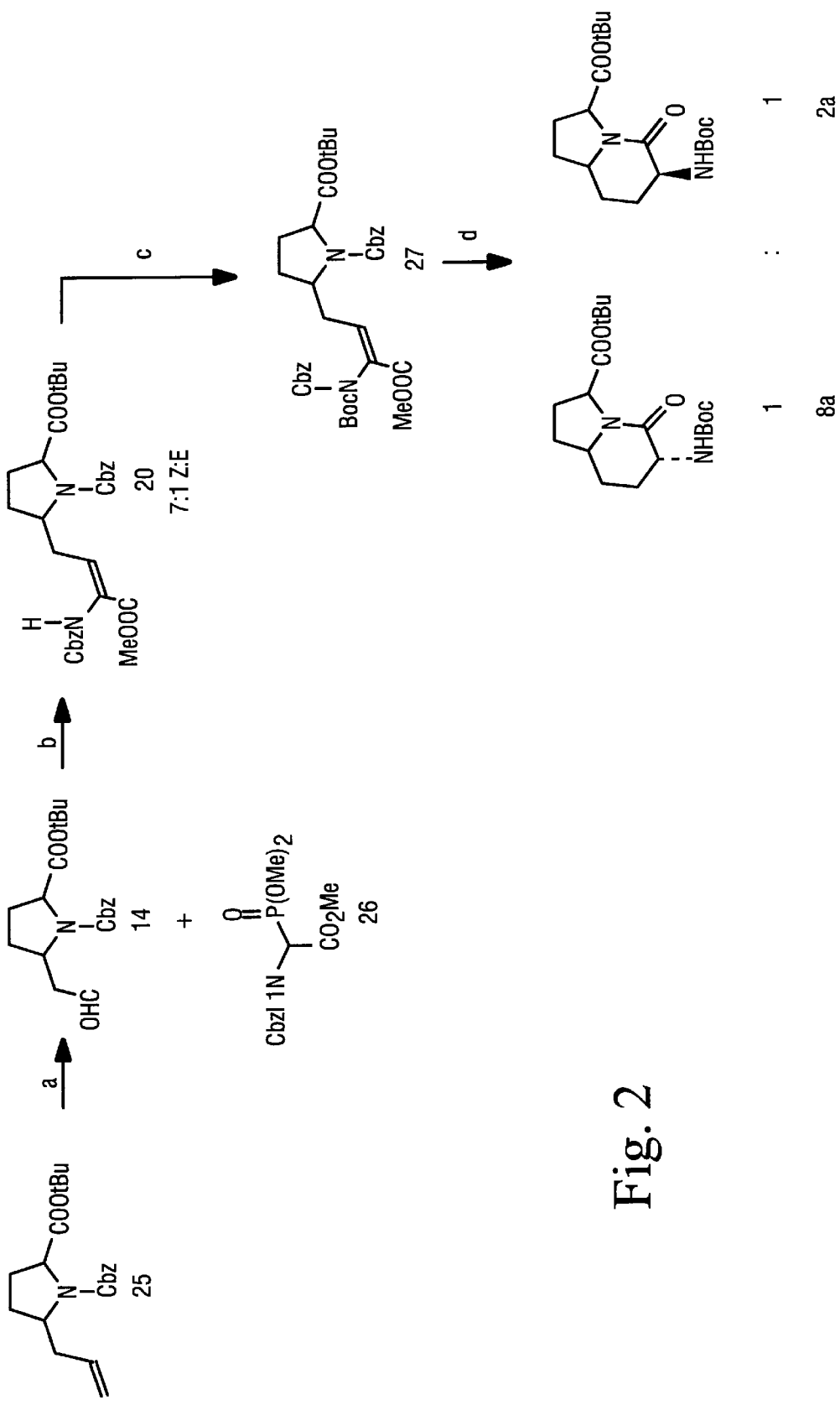
FIG. 2 represents a preferred embodiment of the synthesis of 6,5-fused "cis" lactams.

Examples of bicyclic dipeptide derivatives 1–12 are shown in FIG. 2.

Synthesis of the Fused Bicyclic Lactams 1–12

The synthesis of lactams 1–12 follows the common steps reported in FIG. 1. Starting from the cis or trans 5-alkyl proline aldehydes 13–18, a Horner-Emmons olefination with the potassium enolate of (±)-Z-α-phosphonoglycine trimethyl ester (U. Schmidt, A. Lieberknecht, J. Wild, Synthesis 1984, 53–60)sets up the necessary carbon chain. Following protecting group manipulation (vide infra), reduction of the enamino acrylic acids and treatment with condensing agents gives the lactams of both lo the "cis" and "trans" series in good yields.

In all cases where stereoisomeric mixtures of lactams are formed, they can be easily separated by flash chromatography, and their configuration can be assigned with n.O.e, experiments.

Figure 3:
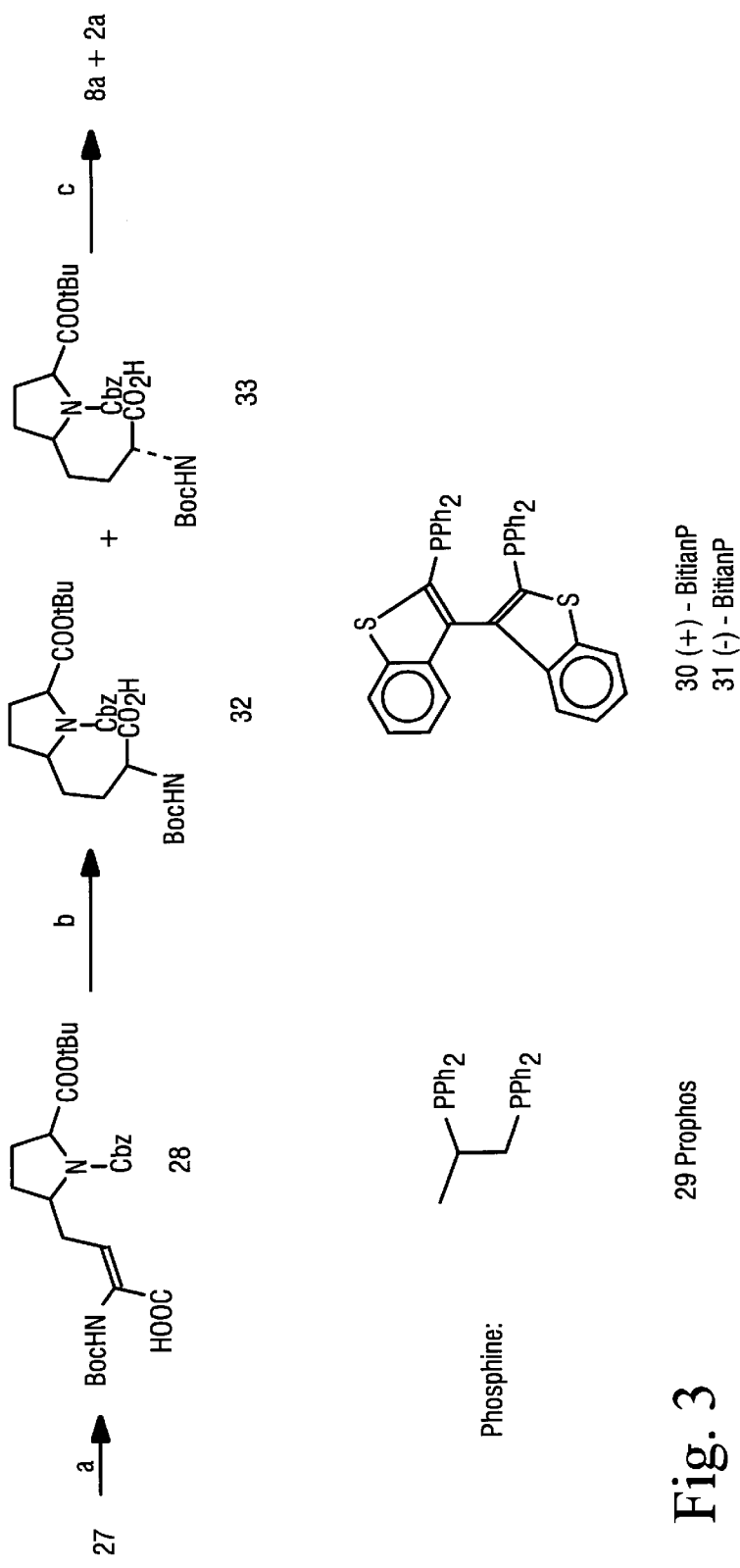
FIG. 3 represents a preferred embodiment of stereoselective hydrogenation with chiral phosphine-Rh catalyst.

The synthetic scheme is best illustrated by the synthesis of the 6,5-fused "cis"-lactams 2a and 8a (FIG. 3). The necessary cis aldehyde 14 is obtained from the known cis 5-allyl-proline derivative 25 (M. V. Chiesa, L. Manzoni, C. Scolastico, Synlett 1996, 441–443) and reacted with the commercially available phosphonate 26 (U. Schmidt, A. Lieberknecht, J. Wild, Synthesis 1984, 53–60) to give 20 in 98% yield and 7:1 Z:E ratio, Hydrogenation of 20 occurs initially at the enamino Cbz group, and thus results in a complex mixture of products. To circumvent this problem, the substrate is treated with $Boc_2O$ to give 27 (98%). Reduction of 27 with $H_2/Pd(OH)_2$ followed by reflux in MeOH gives a 1:1 mixture of 8a and 2a, which are easily separated by flash-chromatography. From 14 the whole sequence requires only two chromatographic separations (purification of 20 and separation of 8a from 2a) and can easily be carried out in multigram scale.

The stereoselective preparation of the two epimers 8a and 2a (FIG. 3) is carried out using chiral phosphine-Rh catalysed hydrogenation of the enamino acid 28.

Chiral phosphine-Rh catalyst is well-known to represent a powerful and well-established way of access to naturally and non-naturally occurring amino acids and the catalytic asymmetric hydrogenation of dehydropeptides is the logical extension of this methodology to the preparation of biologically active chiral oligo- and polypeptides In asymmetric catalytic hydrogenations using chiral phosphine-Rh catalysts (Z) olefins usually gives the highest stereoisomeric purity of the products, but the most stringent requirement for the substrate remains the presence of an acetamido or an equivalent group on the double bond. (K. E. Koenig in Asymmetric Synthesis, J. D. Morrison Editor, Vol 5, Academic Press Inc. 1985, 71) The amide-type carbonyl is needed in order to allow two-point co-ordination of the substrate to the metal, which increases the sterical demand as it has been fully elucidated experimentally.( J. Halpern, ibidem, 41) For applications to the synthesis of peptides protecting groups other than the acetamido, like Boc or Cbz should be used, thus permitting differential deprotection. However, very few examples of asymmetric catalytic hydrogenation are known in which these protecting groups are found on the enamino nitrogen: (B. Basu, S. K. Chattopadhyay, A. Ritzen, T. Frejd, Tetrahedron Asymmetry, 1997, 8, 1841) (S. D. Debenharn, J. D. Debenham, M. J. Burk, E. J. Toone, J.Am.Chem.Soc. 1997, 119, 9897) more frequently Boc or Cbz protecting groups are present in different position of dehydropeptides being hydrogenated at the N-terminus. (A Hammadi et al. Tetrahedron Lett. 1998, 39, 2955—I. Ojima, Pure & Appl. Chem. 1984, 56, 99). For the catalytic asymmetric hydrogenation of 28 [Rh (Phosphine)(COD)]$ClO_4$ catalysts is used. The catalysts were prepared by displacing one cyclooctadiene ligand of [Rh(COD)$_2$]$ClO_4$ with the appropriate phoaphine. The ligands investigated are (R)-Prophos 29 and (+) or (−) BitianP 30 and 31. BitianP is a chiral atropisomeric chelating phosphine belonging to a new class of ligands based on biheteroaromatic framework, which gives very high e.e. % in the asymmetric hydrogenation of olefins and ketones. (E. Cesarotti et al. J.Chem.Soc.Chem.Comm. 1995, 685— Cesarotti et al. J.Org.Chem. 1996, 61, 6244).

The results of asymmetric hydrogenation are reported in the Table 1. The conversion is always quantitative but the highest stereodifferentiation is obtained with [Rh/(−)-BitianP] (entry 3) The results suggest that the newly created stereocentre is mainly determined by the catalyst, which overruns the effect of the stereocentre on the substrates (entry 2 and 3). The results also indicate that the Boc protecting group on the enamino nitrogen fulfils the requirements and allows the olefin to chelate to the catalyst.

TABLE 1

Asymmetric hydrogenation of 28

| Entry | Catalyst | 32/33 | d.e. % |
|---|---|---|---|
| 1 | Rh-29 | 86/14 | 72 |
| 2 | Rh-30 | 13/87 | 74 |
| 3 | Rh-31 | 90/10 | 80 |

Reactions were carried out at R.T. for 24 h under 10 atm of $H_2$

Treatment of crude 32 and 33 with $CH_2N_2$, followed by hydrogenation and cyclisation under the usual conditions ($H_2$/Pd—C followed by reflux in MeOH) allows a stereoselective route to lactams 8a and 2a.

Figure 4:
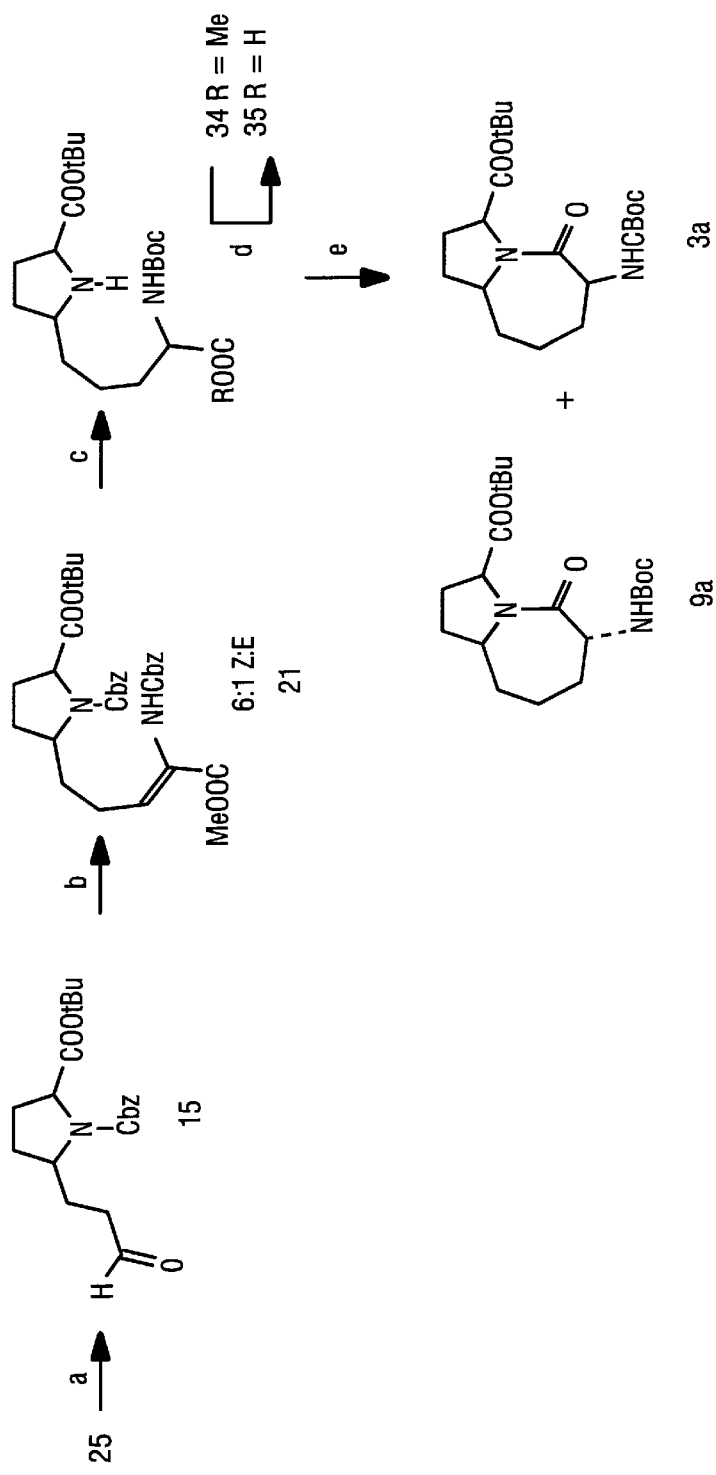
FIG. 4 represents a preferred embodiment of the synthesis of 7,5-fused "cis" lactams.

All the remaining lactams 1–12 can be synthesised following essentially the same sequence described above. Thus, the 7,5-fused lactams 3a and 9a (FIG. 4) can be made starting from the cis aldehyde 15, easily prepared from the cis 5-allyl proline 25.( M. V. Chiesa, L. Manzoni, C. Scolastico, Synlett 1996, 441–443) Horner-Emmons reaction of 15 with 26 gives a 6:1 Z:E mixture of enamino acrylates. After N-protection they are reduced with $H_2$/Pd—C. The thermic cyclisation of methyl ester 34 can be carried out n a suitable solvent, for example xylene. Better results are obtained upon ester hydrolysis followed by EDC/HOBT promoted lactam formation to give 3a and 9a, which are easily separable by flash chromatography (51% overall yield from 25).

Figure 5:
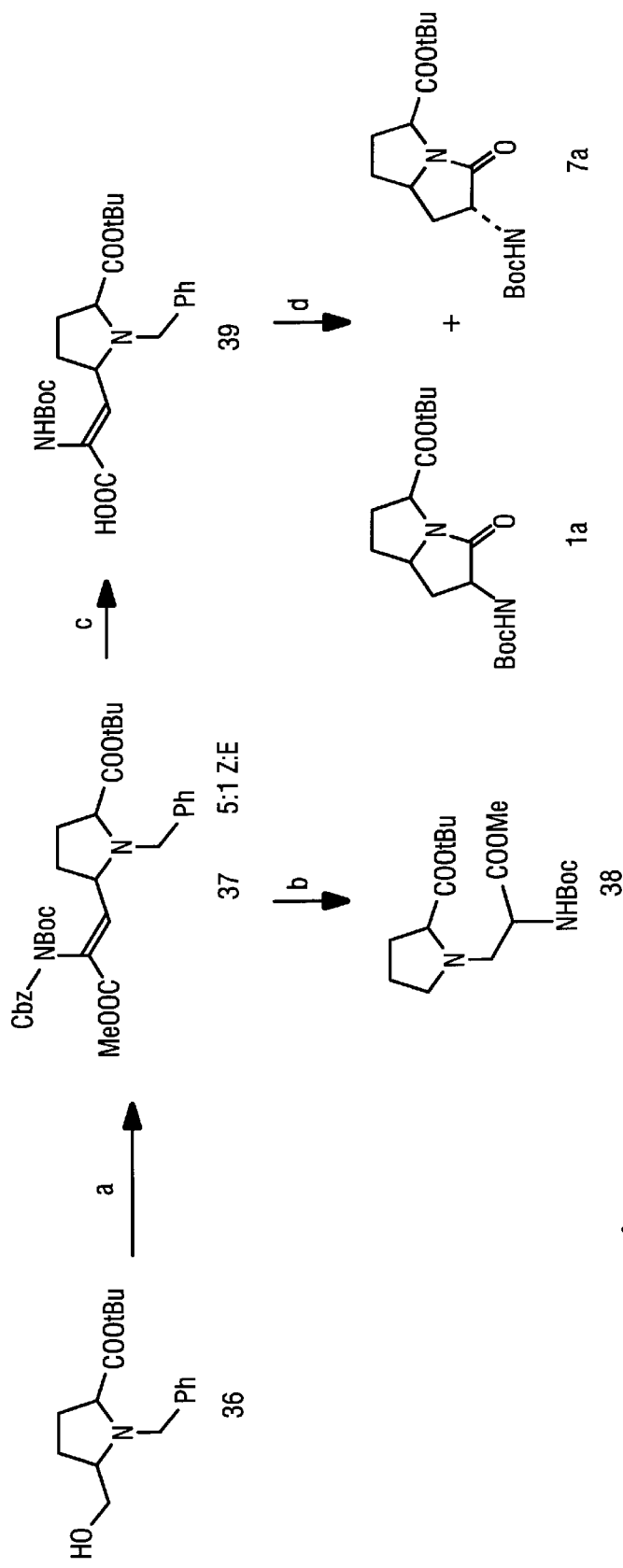
FIG. 5 represents a preferred embodiment of the synthesis of 5,5-fused "cis" lactams.

The starting material for the synthesis of the 5,5-fused "cis" lactams (FIG. 5) is alcohol 36. Oxidation and Horner-Emmons reaction with 26 followed by N-Boc protection gives 37 as a 5:1 Z:E mixture in 57% yield. Hydrogenation of 37 ($H_2$/Pd(OH)$_2$) results in a complex mixture of products, from which the 1,2 diamino ester 38 is anyway isolated in 40% yield. The formation of 38 may result from initial N-debenzylation of 37 followed by intramolecular Michael addition to the enamino ester double bond and hydrogenolysis of the resulting aziridine. The problem can be partly circumvented by performing the hydrogenation starting from the acid 39. Treatment of 39 with $H_2$/Pd—C followed by reflux in MeOH gives an easily separable 1:1 mixture of 1a and 7a in 40% yield.

Figure 6:
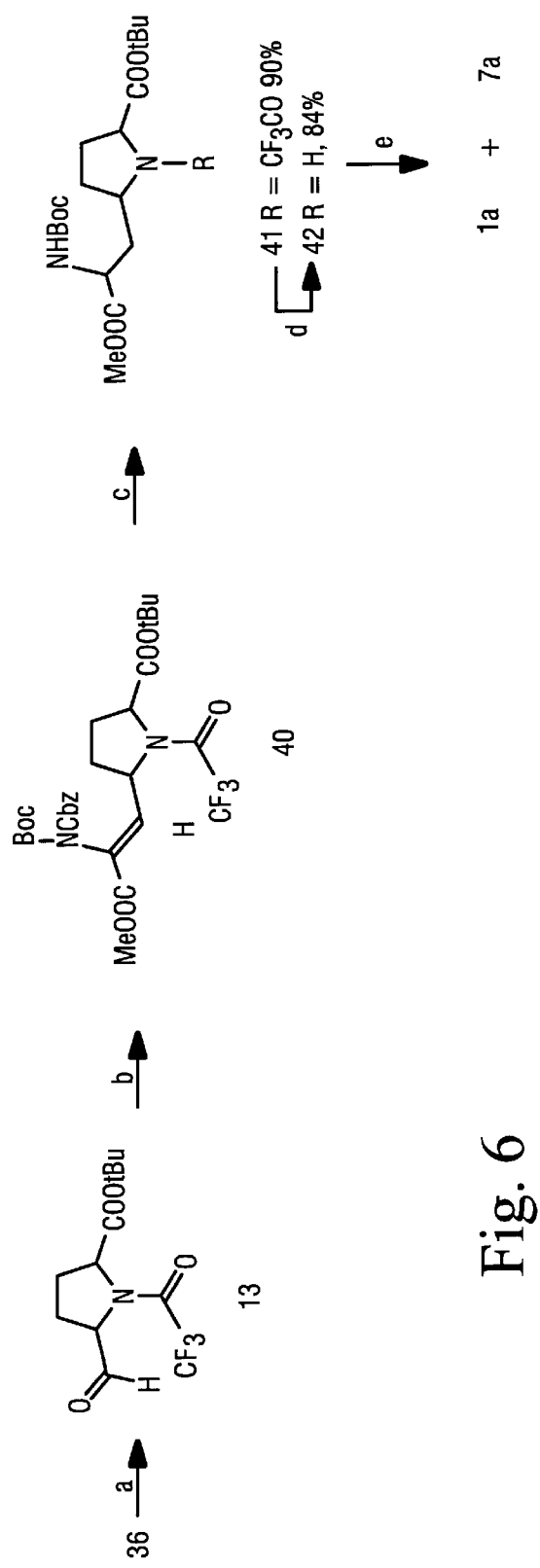
FIG. 6 represents another preferred embodiment of the is synthesis of 5,5-fused "cis" lactams.

An alternative synthesis of these lactams is also provided starting from the trifluoroacetamido aldehyde 13 (FIG. 6). Aldehyde 13 is synthesised from 36 with a series of 5 high-yielding steps. Horner-Emmons and nitrogen protection gives 40 (46% over 7 steps), which could be directly reduced to give a 1:1 mixture of the fully protected ester 41 (77%). Removal of the trifluoroacetamido protecting group ($NaBH_4$ in MeOH, 84%) followed by treatment in refluxing xylene gives the lactams 1a and 7a in 78% yield.

The same synthetic schemes are equally adopted for the synthesis of the "trans" lactam series.

Starting material for the 6,5-fused "trans" lactams 5a and 11a is the trans-substituted proline 17 (FIG. 7). Aldehyde 17 is best obtained from ester 43, which is made in one step from N-Cbz-5-hydroxy proline tert-Butyl ester as 4:1 trans:cis mixture, following a published procedure. (I. Collado et al., Tetrahedron Lett., 1994, 43, 8037) The Horner-Emmons reaction with the potassium enolate of 26 proceeds with 98% yield. Treatment with $Boc_2O$ and cis/trans isomers separation, followed by unselective $H_2$/Pd—C hydrogenation of the crude and treatment in refluxing MeOH gives a 1:1 mixture of easily separated 5a and 11a.

Finally, synthesis of the 7,5-fused "trans" lactams 6a and 12a is achieved starting from the "trans" allyl proline 45 (FIG. 8). (M. V. Chiesa et al. Synlett 1996, 441–443) Hydroboration and Swern oxidation (80% over 2 steps) gives the aldehyde 18, which reacted with 26 to give, after nitrogen protection, 46 as a 6:1 Z:E mixture. The usual sequence (NaOH; $H_2$/Pd—C) allowed the isolation of 6a and 12a in 40% overall yield.

As far as the synthesis of the cyclic RGD portion, synthetic methods are well known in the art. It is convenient to use the solid phase synthesis approach, although other methods could be used.

The classical solid-phase synthesis is preferred.

The solid-phase synthesis is carried out as outlined in C. Gennari et al. Eur.J.Org. Chem. 1999, 379–388.

The protected amino acid is condensed on a suitable resin, for example a Wang-Merrifield resin. Protecting groups are known in this art. 9-fluorenylmethoxycarbonyl (FMOC) is preferred After having activated the resin, N-FMOC-Gly is attached to the Wang-Merrifield resin by means of a suitable condensing agent, preferably diisopropylcarbodiimide (DIC)/1-hydroxybenzotiazole (HOBt)/4-dimethylaminopyridine (DMAP) (J.Org. Chem, 1996, 61, 6735–6738.

Subsequently, N-FMOC-Arg(Pmc)OH is attached, followed by the bicyclic N-FMOC-lactam (IIIa) or (IIb) and finally N-FMOC-Asp(tBu)OH.

The compounds of the present invention are endowed with interesting physiological properties, which make them useful as medicaments. In particular, the compounds of formula (I) herein disclosed are selective antagonists of $\alpha_v\beta_3$ integrins. This antagonist activity provides the use of said compounds for the preparation of medicaments useful in inhibiting the action of $\alpha_v\beta_3$ integrins. In particular, said medicaments will be used in the treatment of tumors, namely in inhibiting tumor growth and/or angiogenesis or metastasis.

As far as the industrial aspects of the present invention are concerned, the compounds of formula (I) shall be suitably formulated in pharmaceutical compositions. Said compositions will comprise at least one compound of formula (I) in admixture with pharmaceutically acceptable vehicles and/or excipients. According to the therapeutic necessity, the bioavailability of the selected compound, its physico-chemical characteristics, the pharmaceutical compositions according to the present invention will be administered by enteral or parenteral route. Enteral pharmaceutical compositions may be both in the liquid or solid from, for example tablets, capsules, pills, powders, sachets, freeze dried powders to be readily dissolved or in any other way soluble powders, solutions, suspensions, emulsions, Parenteral formulation will be in injectable form, as solutions, suspensions, emulsions or in powdery form to be dissolved immediately before use. Other administration routes are also provided, for example intranasal, transdermal or subcutaneous implant. Special pharmaceutical compositions can also be provided. For example controlled release formulations or particular vehicles, for example liposomes.

The preparation of the pharmaceutical compositions according to the present invention is absolutely within the general knowledge of the person skilled in this art.

The dosage will be established according to the type of the pathology to be treated, its severity, and the conditions of the patient (weight, age, and sex).

The following examples further illustrate the invention.

General: $^1H$ and $^{13}C$ NMR spectra were recorded in $CDCl_3$ or $C_6D_6$ as indicated, at 200 (or 300) and 50.3 MHz, respectively. The chemical shift values are given in ppm and the coupling constants in Hz. Optical rotation data were obtained on Perkin-Elmer model 241 polarimeter. Thin-layer chromatography (TLC) is 20 carried out using Merck precoated silica gel F-254 plates. Flash chromatography is carried out with Merck Silica Gel 60, 200–400 mesh. Solvents were dried with standard procedure, and reactions requiring anhydrous conditions were performed under a nitrogen atmosphere. Final product solutions were dried over $Na_2SO_4$, filtered and evaporated under reduced pressure on a Buchi rotary evaporator.

EXAMPLE 1

Preparation of Enamides Via Horner-Emmons Reaction

General procedure A: To a stirred solution of tBuOK (7.36 mmol) in 40 ml of dry $CH_2Cl_2$ under nitrogen atmosphere, at −78° C., was added a solution of Z-α-phosphonoglycine trimethyl ester 26 (7.36 mmol) in 5.0 ml of dry $CH_2Cl_2$. The solution was stirred for 30 min at this temperature and then a solution of aldehyde (6.13 mmol) in dry $CH_2Cl_2$ (25 ml) was added. After 5 hours the solution was neutralised with a phosphate buffer. The aqueous phase was extracted with $CH_2Cl_2$, dried over $Na_2SO_4$ and the solvent evaporated under reduced pressure. The crude was purified by flash chromatography (hexane/ethyl acetate), affording the enamide in a Z:E diastereoisomeric mixture.

Preparation of N-Boc-protected Enamide

General procedure B; A solution of enamide (11.0 mmol), $(BOc)_2O$ (22.0 mmoll and a catalytic quantity of DMAP in 40 ml of dry THF, was stirred for 30 min. under nitrogen. The solution was then quenched with 40 ml of water and extracted with ethyl acetate. The organic phase was dried over $Na_2SO_4$ and the solvent evaporated under reduced pressure. The crude was purified by flash chromatography (hexane/ethyl acetate), yielding the Boc-protected enamide.

Preparation of Alcohol Via Hydroboration

General procedure C: To a solution of allyl proline (2.34 mmol) in dry THIF (4.2 ml) was added a 0.5 M solution of 9-BBN in THF (1.26 mmol). The reaction was stirred for 12 h. and then cooled at 0° C. and, water (0.6 ml), a 3 N solution of NaOH (0.5 ml) and $H_2O_2$ 30% (0.44 ml) were added. The reaction was stirred for 1 h. at room temperature and then refluxed for other 2 h. The aqueous phase was extracted with AcOEt, the collected organic phases were dried over $Na_2SO_4$, filtered and evaporated under reduced pressure, the crude was purified by flash chromatography (hexane/ethyl acetate), yielding the alcohol as yellow oil.

Preparation of Aldehyde Via Swern Oxidation

General procedure D: To a stirred solution of oxalyl chloride (16.9 mmol) in 35 ml of $CH_2Cl_2$, cooled at −60° C., were added DMSO (23.1 mmol), alcohol (5.66 mmol) dissolved in 21 ml of $CH_2Cl_2$, TEA (28.2 mmol). The reaction was warmed at room temperature. After one hour the reaction was washed with 50 ml of water and the aqueous phase was extracted with $CH_2Cl_2$. The collected organic layers were dried over $Na_2SO_4$. The solvent was evaporated under reduced pressure and the crude purified by flash chromatography (hexane/ethyl acetate), yielding the aldehyde.

EXAMPLE 2

Aldehyde (14)

A stirred solution of 25 (6.0 g, 17.4 mmol) in 84 ml of $CH_2Cl_2$ was cooled at −60° C. and bubbled with $O_3$ (flow rate=30 l/hour). After 1.5 hours the reaction was allowed to warm to room temperature and bubbled with $N_2$ in order to eliminate the excess of $O_3$. The solution was then cooled at 0° C. with an ice bath and $Me_2S$ (101.8 mmol, 38 ml) was added. After 5 days of stirring at room temperature the solvent was evaporated under reduced pressure and the crude was purified by flash chromatography (hexane/ethyl acetate, 8:2), yielding 4.53 g of 14 (75%) as yellow oil. -$[\alpha]_D^{22}$=−22.03 (c=1.27, $CHCl_3$). -$^1H$ NMR (200 MHz, $CDCl_3$), (signals were splitted for amidic isomerism): δ=1.4–1.5 [2 s, 9H. $C(CH_3)_3$], 1.6–2.4 (m, 4H, $CH_2$—$CH_2$), 2.4–3.2 (2 m, 2H, $CH_2CHO$), 4.3–4.5 (m, 2H, $CH_2$—CH—N, N—CH—COOtBu), 5.15 (s, 2H, $CH_2Ph$), 7.30 (m, 5H, aromatic), 9.8 (2 s, 1H, CHO). -$^{13}C$ NMR (50.3 MHz, $CDCl_3$) (signals were splitted for amidic isomerism): δ=200.8, 171.7, 154.0, 136.2, 128.3, 128.0, 127.8, 127.6, 81.4, 67.0, 66.9, 60.8, 60.3, 54.0, 53.2, 49.0, 48.3, 31.0, 30.2, 29.5, 28.9, 28.0, 27.7. -$FAB^+MS$: calcd. for $C_{19}H_{25}NO_5$ 347.4, found 348.

EXAMPLE 3
Enamide (20)

The general procedure A was followed using 14 and the crude was purified by flash chromatography (hexane/ethyl acetate, 65:35), affording 20 (98%) in a 7:1 Z.,E ratio as colourless oils. Z-isomer: -$[\alpha]_D^{22}$=+38.78 (c=1.26, $CHCl_3$). -$^1H$ NMR (200 MHz, $CDCl_3$) (signals were splitted for amidic isomerism): δ=1.3–1.5 [2 s, 9H, $C(CH_3)_3$], 1.5–2.3 (m, 4H, $CH_2$—$CH_2$), 2.4–2.7 (2m, 2H, =CH—$CH_2$), 3.7 (2 s, 3H, $COOCH_3$), 4.2 (2 m, 2H, —$CH_2$—CH—N, N—CH—COOtBu), 5.10 (m, 4H, $CH_2Ph$), 6.15 (m, 1H, $CR_2$=CH), 7.30 (m, 10H, aromatic). -$^{13}C$ NMR (50.3 MHz, $CDCl_3$) (signals were splitted for amidic isomerism): δ=172.4, 164.9, 154.5, 136.2, 132.5, 128.3, 128.2, 127.8, 127.7, 127.6, 81.8, 67.2, 66.9, 60.8, 60.3, 57.9, 57.2, 52.1, 33.8, 33.2, 30.7, 29.8, 29.5, 29.0, 28.0, 27.7, 27.6. -$FAB^+$ MS: calcd. for $C_{30}H_{36}N_2O_8$ 552.6, found 553. -E-isomer: -$[\alpha]_D^{22}$=−4.08 (c=1.17, $CHCl_3$). -$^1H$ NMR (200 MHz, $CDCl_3$) (signals were splitted for amidic isomerism): δ1.25–1.50 [3 s, 9H, $C(CH_3)_3$], 1.5–2.3 (m, 4H, $CH_3$—$CH_3$), 2.8–3.3 (2 m, 2H, =CH—$CH_2$), 3.8 (2 s, 3H, $COOCH_3$), 4.1 (m, 1H, —$CH_2$—CH—N), 4.25 (m, 1H, N—CH—COOtBu), 5.15 (2 s, 4H, $CH_2Ph$), 6.30 (m, 1H, =CH), 7.30 (m, 10H, aromatic). -$^{13}C$ NMR (50.3 MHz, $CDCl_3$) (signals were splitted for amidic isomerism): δ=171.8, 164.4, 154.1, 153.6, 136.4, 135.9, 128.7, 128.4, 128.2, 128.1, 128.0, 127.8, 127.7, 127.6, 126.5, 125.9, 81.2, 80.9, 66.7, 61.0, 60.6, 60.2, 58.8, 58.1, 52.2, 32.7, 32.0, 31.8, 29.9, 29.5, 29.2, 28.8, 27.8, 27.7, 22.5, 14.0.

EXAMPLE 4
Enamide (27)

The general procedure B was followed using 20 and the resulting crude was purified by flash chromatography (hexane/ethyl acetate, 7.3), yielding 27 (98%) as yellow oil. -Z-isomer: -$[\alpha]_D^{22}$=+16.95 (c=1.86, $CHCl_3$). -$^1H$ NMR (200 MHz, $CDCl_3$) (signals were splitted for amidic isomerism): δ=1.3–1.5 [2 s, 18H, $C(CH_3)_3$], 1.6–2.2 (m, 4H, $CH_2$—$CH_2$), 2.3–2.8 (2 m, 2H, =CH—$CH_2$), 3.7 (s, 3H, $COOCH_3$), 4.1–4.2 (2 m, 2H, =CH—$CH_2$—CH—N, N—CH—COOtBu), 5.15 (m, 4H, $CH_2Ph$), 6.95 (dd, J=8.5, J=6.4 Hz, 1H, =CH), 7.30 (m, 10H, aromatic). -$^{13}C$ NMR (50.3 MHz, $CDCl_3$) (signals were splitted for arnidic isomerism): δ=171.4, 163.8, 154.6, 154.3, 152.1, 150.4, 139.0, 138.8, 136.2, 135.1, 129.7, 128.3, 128.2, 128.1, 127.8, 127.6, 83.3, 81.2, 77.1, 68.2, 66.8, 60.9, 60.4, 57.5, 56.7, 52.1, 32.8, 32.1, 29.9, 29.1, 28.8, 27.7. -E-isomer: -$[\alpha]_D^{22}$=+7.34 (c=1.33, $CHCl_3$). -$^1H$ NMR (200 MHz, $CDCl_3$) (signals were splitted for amidic isomerism): δ=1.3–1.5 [2 s, 18H, $C(CH_3)_3$], 1.6–2.2 (m, 4H, $CH_2$—$CH_2$), 3.0–3.3 (m, 2H, =CH—$CH_2$), 3.75 (2 s, 3H, $COOCH_3$), 4.1–4.2 (2 m, 2H, =CH—$CH_2$—CH—N, N—CH—COOR), 5.1–5.2 (m, 4H, $CH_2Ph$), 6.3 (m, 1H, =CH), 7.30 (m, 10H, aromatic). -$^{13}C$ NMR (50.3 MHz, $CDCl_3$) (signals were splitted for amidic isomerism): δ=171.6, 163.8, 154.5, 154.3, 152.1, 150.4, 142.8, 142.5, 136.3, 135.2, 128.7, 128.3, 128.2, 128.1, 127.9, 127.8, 127.6, 83.2, 81.1, 68.2, 66.8, 61.1, 60.6, 58.1, 57.4, 51.7, 32.7, 32.0, 29.5, 29.4, 28.9, 28.7, 27.7.

EXAMPLE 5
6,5-Fused Bicyclic Lactam (2a, 8a)

A solution of 0.320 g of 27 (0.49 mmol) and a catalytic quantity of Pd/C 10% in 5 ml of MeOH was stirred under $H_2$ for one night. The catalyst was then filtered through celite and the filtration bed was washed with MeOH. The solvent was evaporated under reduced pressure, the residue was dissolved in MeOH and refluxed for 48 h. The solvent was removed and the two diastereoisomers formed were separated by flash chromatography (hexane/ethyl acetate, 7:3), yielding 0.122 g of 8a and 2a (70%) in a 1.4:1 diastereoisomeric ratio as white foam. -$[\alpha]_D^{22}$=−10.70 (c=1.29, $CHCl_3$). -$^1H$ NMR (200 MHz, $CDCl_3$): δ=1.43–1.45 [2 s, 18H, $C(CH_3)_3$], 1.5–2.5 (m, 8H, $CH_2$—$CH_2$, BocN—CH—$CH_2$—$CH_2$), 3.69 [m, 1H, CH—N], 4.1 (m, 1H, CH—NBoc), 4.38 (dd, J=7.7 Hz, J=1.8 Hz, 1H, N—CH—COOtBu), 5.59 (d, J=5.4 Hz, 1H, NH). -$^{13}C$ NMR (50.3 MHz, $CDCl_3$): δ=170.7, 165.8, 155.8, 147.1, 81.4, 79.3, 59.0, 56.2, 49.9, 32.0, 29.5, 29.1, 28.2, 27.8, 27.0, 26.5. -$FAB^+MS$: calcd. for $C_{18}H_{32}N_2O_5$ 354.46, found 354. -8a -$[\alpha]_D^{22}$=−45.07 (c=1.69, $CHCl_3$), -$^1H$ NMR (200 MHz, $CDCl_3$): δ=1.44–1.46 [2 s, 18H, $C(CH_3)_3$], 1.55–2.2 (m, 7H, $CH_2$—$CH_2$, BocN—CH—CHH—$CH_2$), 2.5 (m, 1H, BocN—CH—CHH), 3.75 [tt, J=11.2 Hz, J=4.2 Hz, 1H, CH—N], 3.90 (m, 1H, CH—NBoc), 4.32 (d, J=9.2 Hz, 1H, N—CH—COOtBu), 5.59 (broad, 1H, NH). -$^{13}C$ NMR (50.3 MHz, $CDCl_3$): δ=170.6, 167.9, 155.7, 81.2, 79.4, 77.5, 60.4, 59.0, 52.2, 31.4, 28.5, 28.3, 28.2, 27.8, 27.6. -$FAB^+MS$: calcd. for $C_{18}H_{32}N_2O_5$ 354.46, found 354.

Acid (28)

To a solution of 27 (0.640 g, 0.980 mmol) in 4.9 ml of MeOH was added 4.9 ml of 1N NaOH (4.9 mmol). After 18 hours of stirring at room temperature the solvent was evaporated under reduced pressure. The solid residue was dissolved in 5 ml of water is and 2N HCl was added until pH 3, then the aqueous solution was extracted with $CH_2Cl_2$. The organic phase was dried with $Na_2SO_4$, the solvent evaporated under reduced pressure and the crude was purified by flash chromatography ($CH_2Cl_2$/MeOH, 95:5), yielding 0.420 g of 28 (85%) as a white solid.

Z isomer: -$[\alpha]_D^{22}$=−57.01 (c=1.99, $CHCl_3$). -$^1H$ NMR (200 MHz, $CDCl_3$) (signals were splitted for amidic isomerism): δ=1.30–1.50 [2 s, 18H, $C(CH_3)_3$], 1.7–2.7 (m, 6H, $CH_2$—$CH_2$, =CH—$CH_2$), 4.2–4.3 (m, 2H, =CH—$CH_2$—CH—N, N—CH—COOtBu), 5.1 (m, 2H, $CH_2Ph$), 6.6 (m, 1H, =CH), 7,30 (m, 6H, aromatic, NHBoc). -$^{13}C$ NMR (50.3 MHz, $CDCl_3$) (signals were splitted for amidic isomerism): δ=171.5, 168.3, 154.8, 154.5, 140.6, 136.4, 136.1, 133.9, 133.5, 128.3, 128.2, 128.1, 127.8, 127.4, 126.9, 81.3, 80.9, 67.1, 66.9, 65.0, 57.5, 56.8, 33.4, 32.4, 29.5, 28.5, 28.5, 28.0, 27.8, 27.7, 27.4.

E isomer: -$[\alpha]_D^{22}$=−41.63 (c=1.87, $CHCl_3$). -$^1H$ NMR (200 MHz, $CDCl_3$) (signals were splitted for amidic isomerism): δ=1.35–1.50 [3 s, 18H, $C(CH_3)_3$], 1.7–2.4 (m, 4H, $CH_2$—$CH_2$), 2.7–3.2 (m, 2H, =CH—$CH_2$), 4.2–4.3 (m, 2H, =CH—$CH_2$—CH—N, N—CH—COOtBu), 5.1 (m, 2H, $CH_2Ph$), 6.7–6.9 (m, 2H, =CH, NHBoc), 7.30 (m, 5H, aromatic). -$^{13}$C NMR (50.3 MHz, CDCl$_3$) (signals were splitted for amidic isomerism): δ=171.7, 167.2, 154.9, 154.5, 154.3, 136.5, 136.2, 128.3, 128.2, 127.7, 127.5, 126.9, 126.3, 126.1, 81.2, 80.4, 66.9, 65.0, 60.7, 60.4, 58.3, 57.7, 32.9, 32.0, 29.5, 28.4, 28.1, 27.8, 27.7, 27.4, 27.1, 14.0.

Acid (32, 33)

To the [Rh-(−)-BitianP] catalyst prepared as described in the literature was added 28 (0.16 mmol) and MeOH (30 ml), the resulting solution was stirred for 30 min. A 200 ml stainless-steel autoclave equipped with a magnetic stirrer and a thermostatic bath was pressurised with hydrogen and vented three times. The solution was transferred into the autoclave with a syringe and the autoclave was pressurised at 10 KPa with hydrogen. The solution was stirred for 24 h. at 30° C. The hydrogen pressure was released, the solvent evaporated. The crude was submitted to the next reaction without further purification.

6,5-fused Bicyclic Lactam (2a)

To a solution of 32 and 33 as diastereomeric mixture in MeOH (1.5 ml) was added a solution of CH$_2$N$_2$ in Et$_2$O until the TLC showed that the reaction was complete. The solution was evaporated and the crude was dissolved in MeOH (2 ml) and a catalytic quantity of Pd/C was added, the mixture was stirred under H$_2$ for 12 h. The catalyst was then filtered through celite pad and washed with MeOH. The solvent was evaporated under reduced pressure and the crude, as a white foam, was refluxed in MeOH for 48 h. The solvent was evaporated under reduced pressure and the crude was purified by flash chromatography (hexane/ethyl acetate 7:3) affording 2a (85%) as a white solid.

EXAMPLE 6

6,5-fused Bicyclic Lactam (8a)

This bicyclic lactam was achieved with the same synthetic sequence followed for the lactam 2a using for the asymmetric hydrogenation the [Rh-(+)-BitianP] catalyst.

Aldehyde (15)

The general procedure C was followed using 25 and the resulting residue was purified by flash chromatography (hexane/ethyl acetate, 7:3), yielding the alcohol (95%) as yellow oil. -$^1$H NMR (200 MHz, CDCl$_3$) δ=1.4 [s, 9H, C(CH$_3$)$_3$], 1.6–2.4 (m, 8H, CH$_2$—CH$_2$), 3.5–3.8 (2 m, 2H, CH$_2$OH), 4.1 (m, 1H, CH$_2$—CH—N), 4.25 (m, 1H, N—CH—COOtBu), 5.15 (s, 2H, CH$_2$Ph), 7.30 (m, 5H, aromatic).

The general procedure D was followed using the previous alcohol and the resulting crude residue was purified by flash chromatography (hexane/ethyl acetate, 7:3), yielding 15 (89%) as an oil. -$^1$H NMR (200 MHz, CDCl$_3$), (signals were splitted for amidic isomerism): δ=1.4–1.5 [2 s, 9H, C(CH$_3$)$_3$], 1.6–2.8 (m, 4H, CH$_2$—CH$_2$), 4.05 (m, 1H, CH$_2$—CH—N), 4.25 (m, 1H, N—CH—COOtBu), 5.15 (s, 2H, CH$_2$Ph), 7.30 (m, 5H, aromatic), 9.6–9.8 (2 s, 1H, CHO).

Aminocater (34)

The general procedure A was followed using 15 and the resulting residue was purified by flash chromatography yielding the enamide (95%) as yellow oil. The compound previously synthesised was submitted to the general procedure B and the resulting residue was purified by flash chromatography yielding the N-Boc protected compound (95%) as white solid. A solution of this compound (0.96 mmol) in MeOH (1 mL) and a catalytic quantity of Pd/C were stirred under hydrogen atmosphere for 12h. The catalyst was then filtered through a celite pad. The solvent was evaporated under reduced pressure yielding 0.320 g of 34 (83%) as a white solid (mixture of two diastereoisomers). -$^1$H NMR (200 MHz, CDCl$_3$): δ=1.47, 1.48 [2 s, 18H, C(CH$_3$)$_3$], 1.40–2.1 (m, 10H, CH$_2$—CH$_2$, BocN—CH—CHH—CH$_2$), 3.00 (m, 1H, CH—N), 3.6 (m, 1H, N—CH—COOtBu), 4.3 (m, 1H, CH—NBoc), 5.05 (db, 1H, NH).

Amino Acid (35)

To a solution of 34 (0.288 g, 0.720 mmol) in MeOH was added 1N NaOH, after 1.5 h. the solution was acidified until pH 3 with 1N HCl, then the solution was evaporated. The crude was submitted to the next reaction without further purification.

EXAMPLE 7

7,5-fused Bicyclic Lactams (3a, 9a)

To a solution of the crude 35 (0.720 mmol) in CH$_2$Cl$_2$ (80 ml) was added in the order: Et$_3$N (0.720 mmol, 0.220 ml), HOBt (0.166 g, 1.22 mmol) and a catalytic quantity of DMAP. After 15 min was added EDC (0.180 g, 0.937 mmol) and the solution was stirred for 24 h. To the solution was added H$_2$O (40 ml), the aqueous phase was extracted with CH$_2$Cl$_2$ and the collected organic layers were dried with Na$_2$SO$_4$ filtered and evaporated under reduced pressure affording 0.191 g of 3a and 9a in a 1:1 diastereoisomeric ratio and 72% of yield over 2 steps.

(3a). -$^1$H NMR (200 MHz, CDCl$_3$): δ=1.41, 1.42 [2 s, 18H, C(CH$_3$)$_3$], 1.5–2.5 (m, 10H, CH$_2$—CH$_2$), 3.80 (m, 1H, CH—N), 4.2 (m, 1H, CH—NBoc), 4.51 (dd, J=4.8 Hz, 1H, N—CH—COOtBu), 5.54 (db, 1H, NH). -(9a). -$^1$H NMR (200 MHz, CDCl$_3$): δ=1.42, 1.43 [2 s, 18H, C(CH$_3$)$_3$], 1.50–2.2 (m, 10H, CH$_2$—CH$_2$), 3.8 [m, 1H, CH—N], 4.25 (dd, J=4.6 Hz, J=9.6 Hz, 1H, CH—NBoc), 4.42 (dd, J=2.3 Hz, J=7.2 Hz, 1H, N—CH—COOtBu), 5.30 (bs, 1H, NH).

Enamide (37): The general procedure D was followed using 36 and the crude was purified by flash chromatography (hexane/ethyl acetate, 7:3), yielding the aldehyde (81%) as an oil. -$^1$H NMR (200 MHz, CDCl$_3$), (signals were splitted for amidic isomerism); δ=1.48 [s, 9H, C(CH$_3$)$_3$], 1.8–2.2 (m, 4H, CH$_2$—CH$_2$), 3.21 (m, 1H, CH$_2$—CH—N), 3.45 (m, 1H, N—CH—COOtBu), 3.70 (d, J=12 Hz, 1H, HCHPh), 4.10 (d, J=12 Hz, 1H, HCHPh), 7.30 (m, 5H, aromatic), 9.12 (d, 1H, CHO).

The general procedure A was followed using the previous aldehyde and the crude was purified by flash chromatography (hexane/ethyl acetate, 65:35), affording the enamide (98%) in a 9:1 Z:E ratio as colourless oils. Z-isomer-$^1$H NMR (200 MHz, CDCl$_3$) δ=1.31 [s, 9H, C(CH$_3$)$_3$], 1.7–2.2 (m, 4H, CH$_2$—CH$_2$), 3.3 (m, 1H, N—CH—COOtBu) 3.5 (s, 1H, CH$_2$—CH—N), 3.66 (d, J=13.2 Hz, HCHPh) 3.73 (s, 1H, COOCH$_3$), 3.79 (d 1H, HCHPh), 5.11 (d, J=12.5 Hz, 1H, OHCHPh), 5.15 (d, J=12.5 Hz, 1H, OHCHPh), 6.07 (d, J=7.4 Hz, 1H, =CH), 7.10–7.6 (m, 10H, aromatic), 8.15 (sb, 1H, —NH). -$^{13}$C NMR (50.3 MHz, CDCl$_3$): δ=173.7, 165.1, 154.1, 137.4, 136.1, 129.5, 128.5, 128.3, 128.0, 127.8, 127.7, 127.1, 80.5, 66.9, 65.3, 62.3, 57.5, 52.0, 30.1, 28.9, 27.7.

The general procedure B was followed using the enamide previous synthesised. The crude was purified by flash chromatography (hexane/ethyl acetate, 7:3) yielding 37 (98%) as a white solid. -$^1$H NMR (200 MHz, CDCl$_3$) (signals were splitted for amidic isomerism): δ=1.3–1.5 [2 s, 18H, C(CH$_3$)$_3$], 1.6–2.2 (m, 4H, CH$_2$—CH$_2$), 3.1 (m, 1H, N—CH—COOtBu), 3.5 (m, 1H, CH$_2$—CH—N), 3.7 (s, 1H, COOCH$_3$), 3.7 (d, J=12 Hz, 1H, HCHPh), 3.9 (d, J=12 Hz, 1H, HCHPh), 5.20 (d, J=12 Hz, 1H, HCHPh), 7.0 (d, J=8.6 Hz, 1H, =CH), 7.1–7.4 (m, 10H, aromatic).

Amino acid (39): To a solution of 37 (0.424 g, 0.713 mmol) in MeOH (4 ml) was added 1N NaOH (4 mmol, 4 ml) and stirred for 1.5 h. The solution was acidified until pH 3 with 1N HCl, then the solution was evaporated. The crude was submitted to the next reaction without further purification. -$^1$H NMR (200 MHz, CDCl$_3$) (signals were splitted for amidic isomerism) δ=1.35, 1.5 [2 s, 18H, C(CH$_3$)$_3$], 1.7–2.3 (m, 4H, CH$_2$—CH$_2$), 3.3 (m, 1H, N—CH— COOtBu), 3.65 (m, 1H, CH$_2$—CH—N), 3.7 (d, J=12.8 Hz, 1H, HCHPh), 3.9 (d, J=12.8 Hz, 1H, HCHPh), 6.5 (d, J=7.6 Hz, 1H, =CH), 7.1–7.4 (m, 10H, aromatic), 9.00 (bs, 1H, —COOH).

EXAMPLE 8
5,5-fused Bicyclic Lactams (1a, 7a)

A solution of 39 (0.713 mmol) and a catalytic quantity of Pd(OH)$_2$/C 20% in 1 ml of MeOH (7 ml) was stirred under hydrogen atmosphere for 12 h. The catalyst was then filtered through a celite pad and the solvent was evaporated under reduced procedure. The crude was dissolved in MeOH and refluxed for 48 h. The solvent was evaporated under reduced pressure and the crude was purified by flash chromatography (hexane/ethyl acetate 6:4) affording 0.097 g of 1a and 7a as a white solid in 40% of yield (over 2 steps) and 1:1 diastereomeric ratio. 1a: -[α]$_D^{22}$=–4.80 (c 1.20, CHCl$_3$). -$^1$H NMR (200 MHz, CDCl$_3$): δ=1.50, 1.51 [2 s, 18H, C(CH$_3$)$_3$], 1.6–2.4 (m, 5H, CH$_2$—CH$_2$, BocN—CH—CHH), 2.95 (m, 1H, BocN—CH—CHH), 3.85 [m, 1H, (CH—N], 4.15 (d, J=8.8 Hz, 1H, N—CH—COOtBu), 4.60 (m 1H, CH—NBoc), 5.25 (broad, 1H, NH). -$^{13}$C NMR (50.3 MHz, CDCl$_3$) (signals were splitted for amidic isomerism): δ=171.7, 169.7, 155.6, 81.8, 79.5, 58.8, 56.5, 56.0, 55.8, 39.5, 33.4, 29.5, 28.2, 27.8. -FAB$^+$MS: calcd. for C$_{17}$H$_{28}$N$_2$O$_5$ 340.41, found 341. -2a: [α]$_D^{22}$=–4.80 (c=1.20, CHCl$_3$). -$^1$H NMR (200 MHz, CDCl$_3$): δ=1.45 [2 s, 18H, C(CH$_3$)$_3$], 1.5–2.5 (m, 6H, CH$_2$—CH$_2$, BocN—CH—CH$_2$), 4.05 (d, J=8.8 Hz, 1H, N—CH—COOtBu), 4.12 (m, 1H, CH—N), 4.25 (m, 1H, CH—NBoc), 5.05 (broad, 1H, NH).- $^{13}$C NMR (50.3 MHz, CDCl$_3$) (signals were splitted for amidic isomerism): δ=170.9, 169.8, 155.2, 82.2, 81.8, 79.9, 77.1, 61.2, 58.8, 57.6, 56.0, 55.8, 34.4, 33.8, 33.4, 29.9, 29.5, 29.2, 28.5, 28.1, 27.7. -FAB$^+$MS. calcd. for C$_{17}$H$_{28}$N$_2$O$_5$ 340.41, found 341.

Aldehyde (13)

To a stirred solution of 36 (1.5 g, 5.14 mmol) in 39 ml of dry CH$_2$Cl$_2$ under nitrogen were added in the order: TBDM-SCl (0.931 g, 6.17 mmol), TEA (6.17 mmol, 0.94 ml) and DMAP (0.063 g, 0.51 mmol). After 12 h. the solvent was evaporated under reduced pressure and the crude purified by flash chromatography (hexane/ethyl acetate, 9:1), yielding 1.910 g of compound (94%) as a colourless oil. -[α]$_D^{22}$=– 3.61 (c=2.52, CHCl$_3$). -$^1$H NMR (200 MHz, CDCl$_3$): δ=–0.5 (s, 6H,CH$_3$Si), 0.85 [s, 9H, (CH$_3$)$_3$C—Si], 1.4 [s, 9H, C(CH$_3$)$_3$], 1.5–2.1 (m, 4H, CH$_2$—CH$_2$), 2.9 (m, 1H, SiO—CH$_2$—CH—N), 3.3–3.4 (m, 3H, N—CH—COOtBu, SiO—CH$_2$), 3.9 (s, 2H, CH$_2$Ph), 7.3 (m, 5H, aromatic). -$^{13}$C NMR (50.3 MHz, CDCl$_3$): δ=173.6, 139.3, 129.1, 127.9, 126.7, 19.9, 67.5, 66.8, 65.8, 58.8, 28.4, 28.0, 27.8, 25.8, 18.1, -3.6.

A solution of the silyl protected alcohol (1.850 g, 4.55 mmol) and Pd(OH)$_2$/C 20% (0.250 g, 0.45 mmol) in 45 ml of MeOH was stirred under hydrogen atmosphere for 4 hours. Then the catalyst was filtered through celite pad and washed with MeOH, the solvent was evaporated under reduced pressure, yielding 1.34 g of hydrogenated compound (94%) as colourless oil. -[α]$_D^{22}$=–5.80 (c=1.99, CHCl$_3$). -$^1$H NMR (200 MHz, CDCl$_3$): δ=0.4 (s, 6H,CH$_3$Si), 0.92 [s, 9H, (CH$_3$)$_3$C—Si], 1.49 [s, 9H, C(CH$_3$)$_3$], 1.5–2.1 (m, 4H, CH$_2$—CH$_2$), 2.35 (broad, 1H, NH), 3.2 (m, 1H, SiO—CH$_2$—CH—N), 3.65 (m, 3H, N—CH—COOtBu, SiO—CH$_2$).

To a stirred solution of the previous compound (1.2 g, 3.79 mmol) in 38 ml of CH$_2$Cl$_2$ were added pyridine (11.39 mmol, 0.92 ml) and (CF$_3$CO)$_2$O (8.35 mmol, 1.16 ml). After 1.5 hours the solvent was evaporated under reduced pressure and the crude purified by flash chromatography (hexane/ethyl acetate, 9:1), yielding 1.4 g of the N-protected pyrrolidine (89%) as colourless oil. -[α]$_D^{22}$=–8.62 (c=2.11, CHCl$_3$). -$^1$H NMR (200 MHz, CDCl$_3$): δ=0.4 (s, 6H,CH$_3$Si), 0.9 [s, 9H, (CH$_3$)$_3$C—Si], 1.47 [s, 9H, C(CH$_3$)$_3$], 1.7–2.4 (m, 4H, CH$_2$—CH$_2$), 3.5 (m, 1H, SiO—CHH), 3.75 (dd, J=10.6 Hz, J=4.2 Hz, 1H, SiO—CHH), 4.2 (m, 1H, SiO—CH$_2$—CH—N), 4.35 (t, J=8.5 Hz 1H, N—CH—COOtBu).

To a stirred solution of N-protected pyrrolidine (1.2 g, 2.91 mmol) in 29 ml of THF, cooled at –40° C., was added a 1M solution of TBAF in THP (3.20 mmol, 3.2 ml). Then the solution was allowed to warm at room temp. After 2.5 hours was added 30 ml of brine and the resulting mixture was extracted with ethyl acetate. The organic phase was dried with Na$_2$SO$_4$ and the solvent evaporated under reduced pressure. The crude was purified by flash chromatography (hexane/ethyl acetate, 6:4), yielding 0.850 g of O-deprotected compound (98%) as colourless oil. -[α]$_D^{22}$=– 6.40 (c=1.45, CHCl$_3$). -$^1$H NMR (200 MHz, CDCl$_3$): δ=1.5 [s, 9H, C(CH$_3$)$_3$], 2.0–2.4 (m, 4H, CH$_2$—CH$_2$), 3.4–3.7 (m, 2H, HO—CH$_2$), 4.2–4.6 (m, 3H, N—CH—COOtBu, HO—CH$_2$—CH—N).

The general procedure D was followed using the alcohol and the residue was purified by flash chromatography (hexane/ethyl acetate, 6:4), yielding the aldehyde (93%) as white solid. -[α]$_D^{22}$=+22.48 (c=1.53, CHCl$_3$). -$^1$H NMR (200 MHz, CDCl$_3$): δ=1.5 [s, 9H, C(CH$_3$)$_3$], 1.8–2.5 (m, 4H, CH$_2$—CH$_2$), 4.5–4.7 (m, 2H, CHO—CH—N, N—CH—COOtBu), 9.7 (s, 1H, CHO).

Enamide (40)

The general procedure A was followed using 13 and the crude residue was purified by flash chromatography affording the enamide (68%) as colourless oil (diastereoisomeric ratio Z:E=1:1). -$^1$H NMR (200 MHz, CDCl$_3$) (signals were splitted for amidic isomerism and were referred to the mixture of two diastereoisomers): δ=1.5 [s, 9H, C(CH$_3$)$_3$], 1.6–2.45 (m, 4H, CH$_2$—CH$_2$), 3.75 (s, 3H, COOCH$_3$), 4.6 (m, 1H, N—CH—COOtBu), 4.8 (dd, J=18 Hz, J=10 Hz, 1H, =CH—CH—N), 5.12 (s, 2H, CH$_2$Ph), 6.3, 6.8 (2 d, J=10 Hz, 1H, =CH of Z-isomer, E-isomer), 7.35 (m, 5H, aromatic), The general procedure B was followed using the enamide and the crude was purified by flash chromatography affording 40 with a 95% of yield as colourless oil. -$^1$H NMR (200 MHz, C$_6$D$_6$) (signals were splitted for amidic isomerism and were referred to the mixture of two diastereoisomers): δ=1.3, 1.5 [2 s, 18H, C(CH$_3$)$_3$], 1.6–2.35 (m, 4H, CH$_2$—CH$_2$), 3.7 (s, 3H, COOCH$_3$), 4.6–4.8 (m, 2H, N—CH—COOtBu, =CH—CH—N), 5.25 (m, 2H, CH$_2$Ph), 7.0 (m, 1H, =CH), 7.35 (m, 5H, aromatic). -$^{13}$C NMR (50.3 MHz, C$_6$D$_6$) (signals were splitted for amidic isomerism and were referred to the mixture of two diastereoisomers): δ=169.1, 163.9, 141.2, 136.1, 129.9, 128.4, 128.2, 127.4, 119.4, 113.7, 83.6, 82.5, 82.0, 68.8, 68.5, 68.2, 62.5, 60.9, 60.8, 58.5, 57.6, 56.8, 53.2, 51.9, 51.7, 51.6, 33.7, 31.8, 30.2, 27.7, 27.5, 26.9.

Aminoester (41)

A Z/E mixture of 40 (0.609 g, 1.01 mmol) and Pd(OH)$_2$/C 20% (0.054 g) in 10 ml of MeOH was stirred under hydrogen atmosphere for 18 h. The catalyst was filtered through a celite pad and washed with MeOH. The solvent was evaporated under reduced pressure and the crude purified by flash chromatography (toluene/Et$_2$O, 85:15), yielding 0.365 g of 40 (77%) as yellow oil. -$^1$H NMR (200 MHz, CDCl$_3$) (signals were splitted for amidic isomerism and were referred to the mixture of two diastereoisomers): δ=1.45 [s, 18H, C(CH$_3$)$_3$], 1.6–2.7 (m, 6H, CH$_2$—CH$_2$, BocN—CH—CH$_2$), 3.75 (2 s, 3H, COOCH$_3$), 4.25–4.4 (2 m, 2H, BocN—CH, BocN—CH—CH$_2$—CH), 4.55 (m, 1H, N—CH—COOtBu), 5.30 (d, J=8.5 Hz, 1H, NH). -$^{13}$C NMR (50.3 MHz, CDCl$_3$) (signals were splitted for amidic isomerism and were referred to the mixture of two diastereoisomers): δ=172.4, 170.0, 155.8, 128.9, 128.0, 82.7, 82.0, 79.7, 61.4, 60.6, 58.0, 56.5, 52.2, 51.5, 37.7, 36.4, 35.5, 30.2, 29.7, 29.0, 28.4, 28.1, 27.6, 25.5. -FAB$^+$MS: calcd. for C$_{20}$H$_{31}$F$_3$N$_2$O$_7$ 468.47, found 468.

Amino acid (42)

A solution of 41 (0.184 g, 0.393 mmol) and NaBH$_4$ (0.0298 g, 0.781 mmol) in 8 ml of MeOH was stirred for 1 hour at room temperature. The solution was concentrated and 10 ml of water was added. The aqueous solution was extracted with ethyl acetate, the collected organic phases were dried on Na$_2$SO$_4$ and the solvent evaporated under reduced pressure. The two diastereoisomers formed in the previous reactions were separated at this step by flash chromatography (ethyl acetate/hexane, 6:4), achieving 0.123 g of 42 (R) and 42 (S) (84%) in a 2.6:1 diastereoisomeric ratio as colourless oil. -42 (R): -$^1$H NMR (200 MHz, C$_6$D$_6$) (signals were splitted for amidic isomerism): δ=1.30, 1.45 [2 s, 18H, C(CH$_3$)$_3$], 1.5–1.9 (m, 6H, CH$_2$—CH$_2$, BocN—CH— CH$_2$), 2.85 (m, 1H, BocN—CH—CH$_2$—CH), 3.2–3.4 (m, 4H, COOCH$_3$, N—CH—COOtBu), 4.65 (m, 1H, BocN—CH), 6.6 (broad, 1H, NHBoc). -$^{13}$C NMR (50.3 MHz, C$_6$D$_6$) (signals were splitted for amidic isomerism): δ=174.1, 173.2, 155.8, 81.4, 81.3, 79.5, 60.6, 60.4, 56.5, 56.3, 52.5, 52.0, 37.7, 31.9, 30.0, 29.8, 28.2, 28.0, 27.9. -FAB$^+$MS: calcd. for C$_{18}$H$_{32}$N$_2$O$_6$ 372.46, found 373. -42 (S): -$^1$H NMR (200 MHz, C$_6$D$_6$) (signals were splitted for amidic isomerism): δ=1.30, 1.50 [2 s, 18H, C(CH$_3$)$_3$], 1.50–1.80 (m, 6H, CH$_2$—CH$_2$, BocN—CH—CH$_2$), 2.8 (m, 1H, BocN—CH—CH$_2$—CH), 3.3 (s, 3H, COOCH$_3$), 3.4 (dd, J=9.1 Hz, J=5.9 Hz, 1H, N—CH—COOtBu), 4.45 (m, 1H, BocN—CH), 5.3 (broad, 1H, NHBoc). -$^{13}$C NMR (50.3 MHz, C$_6$D$_6$) (signals were splitted for amidic isomerism): δ=171.7, 171.5, 164.2, 164.0, 154.7, 154.3, 153.5, 136.6, 136.4, 135.8, 128.4, 128.3, 128.2, 128.1, 127.7, 126.2, 125.9, 125.8, 81.0, 87.1, 66.8, 66.6, 60.8, 60.4, 58.2, 57.5, 52.3, 52.2, 32.8, 31.9, 28.5, 28.1, 27,8, 27.7, 27.4, 27.1. -FAB$^+$MS: calcd. for C$_{18}$H$_{32}$N$_2$O$_6$ 372.46, found 373.

EXAMPLE 9
5,5-Fused Bicyclic Lactam [1a]

A stirred solution of 42 (S) (0.028 g, 0.075 mmol) in 1.5 ml of p-xylene was warmed at 130° C. for 24 hours. The solvent was then evaporated under reduced pressure and the crude purified by flash chromatography (hexane/ethyl acetate, 7:3), yielding 19 mg of 1a (74%) as a white foam. -[α]$_D^{22}$=−4.80 (c=1.20, CHCl$_3$). -$^1$H NMR (200 MHz, CDCl$_3$): δ=1.50, 1.51 [2 s, 18H, C(CH$_3$)$_3$], 1.6–2.4 (m, 5H, CH$_2$—CH$_2$, BocN—CH—CHH), 2.95 (m, 1H, BocN—CH—CHH), 3.85 [m, 1H, (CH—N], 4.15 (d, J=8.8 Hz, 1H, N—CH—COOtBu), 4.60 (m 1H, CH—NBoc), 5.25 (broad, 1H, NH). -$^{13}$C NMR (50.3 MHz, CDCl$_3$) (signals were splitted for amidic isomerism): δ=171.7, 169.7, 155.6, 81.8, 79.5, 58.8, 56.5, 56.0, 55.8, 39.5, 33.4, 29.5, 28.2, 27.8. -FAB$^+$MS: calcd. for C$_{17}$H$_{28}$N$_2$O$_5$ 340.41, found 341.

EXAMPLE 10
5,5-Fused Bicyclic Lactam [17a]

The compound [7a] was achieved from compound 42 (R), by using the same procedure described for the synthesis of compound 1a, with a 65% of yield as white foam. -[α]$_D^{22}$=− 4.80 (c=1.20, CHCl$_3$). -$^1$H NMR (200 MHz, CDCl$_3$): δ=1.45 [2 s, 18H, C(CH$_3$)$_3$], 1.5–2.5 (m, 6H, CH$_2$—CH$_2$, BocN—CH—CH$_2$), 4.05 (d, J=8.8 Hz, 1H, N—CH—COOtBu), 4.12 (m, 1H, CH—N), 4.25 (m, 1H, CH—NBoc), 5.05 (broad, 1H, NH). -$^{13}$C NMR (50.3 MHz, CDCl$_3$) (signals were splitted for amidic isomerism): δ=170.9, 169.8, 155.2, 82.2, 81.8, 79.9, 77.1, 61.2, 58.8, 57.6, 56.0, 55.8, 34.4, 33.8, 33.4, 29.9, 29.5, 29.2, 28.5, 28.1, 27.7. -FAB$^+$MS: calcd. for C$_{17}$H$_{28}$N$_2$O$_5$ 340.41, found 341.

Aldehyde (14, 17)

To a stirred solution of 43 (1.205 g, 3.08 mmol) in dry diethylether (31 mL) at −10° C., LiBH$_4$ 2M in THF (1.5 mL, 3.08 mmol) was added. After 24 h a saturated solution of NaHCO$_3$ (40 ml) was added and the resulting mixture was extracted with AcOEt. The organic phase was dried over Na$_2$SO$_4$ and evaporated to dryness. The crude product was purified by flash chromatography (hexane/ethyl acetate 1:1), yielding 1.01 g of alcohol (94%) as a yellow oil. -Trans-isomer: [α]$_D^{22}$=−32.3 (c=1.02, CHCl$_3$).- $^1$H NMR (200 MHz, CDCl$_3$): δ=1.35 [s, 9H, C(CH$_3$)$_3$], 1.5–2.4 (m, 6H, CH$_2$—CH$_2$, CH$_2$—CH$_2$—O), 3.5–3.7 (m, 2H, CH$_2$OH), 3.82 (bs, 1H, OH), 4.22 (dd, J=7.5, J~0, 1H, CHCO$_2$tBU), 4.38 (m, 1H, CH$_2$—CH—N), 5.15 (m, 2H, CH$_2$Ph), 7.32 (s, 5H, aromatic). -$^{13}$C NMR (50.3 MHz, CDCl$_3$) (signals were splitted for amidic isomerism): δ=171.4, 156.1, 136.0, 128.4, 128.3, 127.9, 127.8, 127.7, 81.2, 81.1 67.2, 67.0, 60.4, 59.9, 59.0, 55.2, 55.1, 38.6, 37.7, 28.9, 28.7, 27.8, 27.7. -Cis-isomer: [α]$_D^{22}$=−54.0 (c=1.51, CHCl$_3$). -$^1$H NMR (200 MHz, CDCl$_3$): δ=1.33 [s, 9H, C(CH$_3$)$_3$], 1.4–1.24 (m, 6H, CH$_2$—CH$_2$, CH$_2$—CH$_2$—O), 3.6–3.9 (m, 2H, CH$_2$OH), 4.08 (dd, J=9.5, J=4, 1H, OH), 4.25 (dd, J=J 8.5, 1H, CHCO$_2$tBu), 4.40 (m, 1H, CH$_2$—CH—N), 5.15 (m, 2H, CH$_2$Ph), 7.35 (s, 5H, aromatic), -$^{13}$C NMR (50.3 MHz, CDCl$_3$): δ=27.7, 28.9, 30.4, 37.4, 55.4, 58.8, 60.5, 67.4, 81.3, 127.7, 127.9, 128.3, 136.1, 155.9, 171.8.

A solution of the alcohol (0.304 g, 0.87 mmol) in dry CH$_2$Cl$_2$ (2.5 mL) was added to a suspension of Dess-Martin periodinane (0.408 g, 1.13 mmol) in dry CH$_2$Cl$_2$ (2.5 mL) at room temperature. After 1 h Et$_2$O and NaOH 1N were added till clear solution. The aqueous phase was extracted twice with Et$_2$O; the collected organic layers were washed with H$_2$O, dried with Na$_2$SO$_4$, and evaporated to dryness. The crude product was purified by flash chromatography (hexane/ethyl acetate 7:3) affording 0.277 g of 17 (92%). -Trans-isomer: [α]$_D^{22}$−48.65 (c=1.01, CHCl$_3$). -$^1$H NMR (200 MHz, CDCl$_3$) (signals were splitted for amidic isomerism): δ=1.35–1.45 [2 s, 9H, C(CH$_3$)$_3$], 1.6–2.6 (m, 4H, CH$_2$—CH$_2$), 2.8–3.1 (2 m, 2H, CH$_2$CHO), 4.3 (m, 1H, CHO—CH$_2$—CH—N), 4.6 (m, 1H, N—CH—COOR), 5.15 (m, 2H, CH$_2$Ph), 7.30 (m, 5H, aromatic), 9.1, 9.3 (2 m, 1H, CHO). -$^{13}$C NMR (50.3 MHz, CDCl$_3$) (signals were splitted for amidic isomerism): δ=200.3, 171.4, 154.1, 136.2, 128.4, 128.2, 128.0, 127.8, 127.7, 81.3, 67.1, 66.9, 60.5, 60.1, 53.4, 52.5, 49.0, 48.4, 29.5, 28.6, 28.3, 27.8, 27.7, 27.3.

N-Boc-protected enamide (44): The mixture of aldehydes 14 and 17 was reacted following the general procedure A. The crude product was purified by flash chromatography (hexane/ethyl acetate 7:3), affording the enamide in 99% yield, as a trans:cis, Z/E mixture. Trans-Z-isomer : [α]$_D^{22}$=− 61.84 (c=1.01, CHCl$_3$). -$^1$H NMR (200 MHz, CDCl$_3$) (signals were splitted for amidic isomerism); δ=1.35–1.50 [2 s, 9H, C(CH$_3$)$_3$], 1.6–2.3 (m, 4H, CH$_2$—CH$_2$), 2.3–2.8 (2 m, 2H, =CH—CH$_2$), 3.75 (s, 3H, COOCH$_3$), 4.15–4.25 (2 m, 2H, —CH$_2$—CH—N and N—CH—COOtBu), 5.15 (m, 4H, CH$_2$Ph), 6.55 (t, J=8.5 Hz, 1H, =CH), 7.35 (m, 10H, aromatic), -$^{13}$C NMR (50.3 MHz, CDCl$_3$) (signals were splitted for amidic isomerism): δ=171.4, 164.8, 164.6, 154.4, 153.9, 153.7, 136.4, 136.2, 135,9, 135.7, 133.0, 132.0, 128.4, 128.3, 128.2, 128.1, 128.0, 127.9, 127.8, 127.6, 126.7, 81.2, 67.3, 67.2, 67.0, 66.8, 60.6, 60.2, 57.6, 56.7, 52.3, 33.5, 32.5, 28.5, 27.7, 27.4. -FAB⁺MS: calcd. for $C_{30}H_{36}N_2O_8$ 552.6, found 552.

Trans-E-isomer: $[\alpha]_D^{22}$=−50.16 (c=148, CHCl₃). -¹H NMR (200 MHz, CDCl₃) (signals were splitted for amidic isomerism): δ=1.35–1.45 [2 s, 9H, C(CH₃)₃]1.6–2.4 (m, 4H, CH₂—CH₂), 2.7–3.1 (2 m, 2H, =CH—CH₂), 3.8 (2 s, 3H, COOCH₃), 4.1–4.3 (2 m, 2H, —CH₂—CH—N e N—CH—COOtBu), 5.10 (m, 4H, CH₂Ph), 6.50 (m, 1H, =CH), 7.25 (m, 10H, aromatic). -¹³C NMR (50.3 MHz, CDCl₃) (signals were splitted for amidic isomerism); δ=171.7, 171.5, 164.2, 164.0, 154,7, 154.3, 153.5, 136.6, 136.4, 135.8, 128.4, 128.3, 128.2, 128.1, 127.7, 126.2, 125.9, 125.8, 81.0, 87.1, 66.8, 66.6, 60.8, 60.4, 58.2, 57.3, 52.2, 32.8, 31.9, 28.5, 28.1, 27.8, 27.7, 27.4, 27.1.

The mixture of enamides (0.394 g, 0.71 mmol) was reacted following the general procedure B. Flash chromatography of the crude product (hexane/ethyl acetate 75:25) afforded 0.287 g (73%) of pure trans-isomer 23. -Z-isomer: $[\alpha]_D^{22}$=−50.98 (c=1.56, CHCl₃). -¹H NMR (200 MHz, CDCl₃) (signals were splitted for amidic isomerism): δ=1.3–1.5 [4 s, 18H, C(CH₃)₃], 1.7–2.6 (m, 6H, CH₂—CH₂ and =CH—CH₂), 3.7 (s, 3H, COOCH₃), 4.1–4.3 (m, 2H, —CH₂—CH—N and N—CH—COOtBu), 5.15 (m, 4H, CH₂Ph), 6.8 (m, 1H, =CH), 7.30 (m, 10H, aromatic). -¹³C NMR (50.3 MHz, CDCl₃) (signals were splitted for amidic isomerism): δ=171.4, 163.9, 154.6, 154.5, 150.0, 146.2, 138.5, 138.0, 136.2, 129.9, 128.3, 128.2, 128.1, 127.8, 83.4, 81.2, 68.3, 67.0, 66.8, 60.6, 60.2, 56.9, 56.2, 52.2, 32.9, 32.0, 28.3, 27.8, 27.7, 27.3. -FAB⁺MS: calcd. for $C_{35}H_{44}N_2O_{10}$ 652.7, found 652.

E-isomer: ¹H NMR (200 MHz, CDCl₃): δ=1.3–1.4 [2 s, 18H, C(CH₃)₃], 1.5–2.3 (m, 4H, CH₂—CH₂), 3.0 (2 m, 2H, =CH—CH₂), 3.65 (2 s, 3H, COOCH₃), 4.2 (m, 2H, —CH₂—CH—N and N—CH—COOtBu), 5.15 (m, 4H, CH₂Ph), 6.1 (2 t, J=8.5 Hz, 1H, =CH), 7.30 (m, 10H, aromatic). -¹³C NMR (50.3 MHz, CDCl₃): δ=171.5, 163.7, 154.6, 154.3, 152.2, 150.4, 142.7, 142.2, 136.3, 135.1, 128.9, 128.3, 128.2, 128.0, 127.8, 127.7, 83.4, 83.3, 81.1, 77.1, 68.3, 66.9, 66.7, 60.7, 60.3, 57.6, 56.8, 51.7, 32.9, 32.0, 28.4, 28.0, 27.7, 27.3, 27.0.

EXAMPLE 11
6,5 Fused Bicyclic Lactams (5a, 11a)

A solution of 44 (0.489 g, 0.75 mmol) and Pd(OH)₂/C 20% (catalytic) in MeOH (7.5 mL) was stirred under H₂ for one night. The catalyst was filtered off and the mixture was refluxed for 24 h. The solvent was then removed and the two diastereoisomeric products were separated by flash chromatography (hexane/ethyl acetate 6:4), yielding 0.186 g of 5a and 11a (70%) in a 1.4:1 diastereoisomeric ratio. -5a: ¹H NMR (200 MHz, CDCl₃): δ=1.45–1.50 [2 s, 18 H, C(CH₃)₃], 1.55–2.60 (m, 8H, CH₂—CH₂ and BocN—CH—CH₂—CH₂), 3.68 [tt, J=14.9 Hz and 4.2 Hz, 1H, (R)₂CH—N], 4.05 (m, 1H, CH—NBoc), 4.35 (t, J=8.5 Hz, 1H, N—CH—COOtBu), 5.28 (broad, 1H, NH). -FAB+MS: calcd. for $C_{18}H_{32}N_2O_5$ 354.46, found 354.

11a: $[\alpha]_D^{22}$=−107.9 (c=1.7, CHCl₃). -¹H NMR (200 MHz, CDCl₃): δ=1.45–1.50 [2 s, 18H, C(CH₃)₃], 1.75–2.50 (m, 8H, CH₂—CH₂ and BocN—CH—CH₂—CH₂), 3.70 [m, 1H, CH—N], 4.15 (m, 1H, CH—NBoc), 4.50 (t, J=7.0 Hz, 1H, N—CH—COOtBu), 5.55 (broad, 1H, NH). -¹³C NMR (50.3 MHz, CDCl₃): δ=170.6, 168.5, 155.5, 81.4, 79.3, 59.0, 56.2, 49.9, 32.3, 28.1, 27.8, 26.5, 25.9. -FAB+MS: calcd. for $C_{18}H_{32}N_2O_5$ 354.46, found 354.

Aldehyde (18)

The general procedure C was followed using 43 and the crude residue was purified by flash chromatography affording the alcohol with a yield of 98%, -¹H NMR (200 MHz, CDCl₃) δ=1.32 [s, 9H, C(CH₃)₃], 1.4–2.4 (m, 8H, CH₂—CH₂), 3.5–3.7 (m, 2H, CH₂OH), 4.1 (m, 1H, CH₂—CH—N), 4.24 (m, 1H, N—CH—COOtBu), 5.05 (s, 2H, CH₂Ph), 7.25 (m, 5H, aromatic).

The general procedure D was followed using the alcohol and the crude was purified by flash chromatography (hexane/ethyl acetate 6:4) affording 18 with a yield of 82% -¹H NMR (200 MHz, CDCl₃), (signals were splitted for amidic isomerism): δ=1.32, 1.45 [2 s, 9H, C(CH₃)₃], 1.5–2.7 (m, 8H, CH₂—CH₂), 4.1 (m, 1H, CH₂—CH—N), 4.25 (m, 1H, N—CH—COOR), 5.15 (s, 2H, CH₂Ph), 7.20–7.40 (m, 5H, aromatic), 9.6–9.8 (2 m, 1H, CHO).

Enamide (46)

The general procedure A was followed using 18 and the crude was purified by flash chromatography (hexane/ethyl acetate 6:4) affording the enamide with a yield of 90% (diastereomeric ratio Z/E=7:1) -¹H NMR (200 MHz, CDCl₃), (signals were splitted for amidic isomerism): δ=1.32, 1.42 [s, 9H, C(CH₃)₃], 1.5–2.7 (m, 8H, CH₂—CH₂), 3.71 (s, 1H, COOCH₃), 4.1 (m, 1H, CH₂—CH—N), 4.22 (m, 1H, N—CH—COOtBu), 5.0–5.20 (m, 4H, CH₂Ph), 6.6 (m, 1H, =CH), 7.20–7.45 (m, 10H, aromatic).

The general procedure B was followed using the enamide and the crude residue was purified by flash chromatography yielding 46 (98%). -¹H NMR (200 MHz, CDCl₃), (signals were splitted for amidic isomerism): δ=1.32, 1.42 [2 s, 18H, C(CH₃)₃], 1.5–2.2 (m, 8H, CH₂—CH₂), 3.71 (s, 1H, COOCH₃), 3.9 (m, 1H, CH₂—CH—N), 4.22 (m, 1H, N—CH—COOtBu), 5.0–5.20 (m, 4H, CH₂Ph), 6.9 (m, 1H, =CH), 7.20–7.45 (m, 10H, aromatic). -¹³C NMR (50.3 MHz, CDCl₃) (signals were splitted for amidic isomerism): δ=141.6, 128.4, 128.2, 128.1, 127.8, 127.7, 68.2, 66.8, 60.5, 58.1, 52.1, 31.3, 29.5, 27.1, 27.3, 24.6.

EXAMPLE 12
Trans-7,5-fused Bicyclic Lactam (6a, 12a)

To a solution of 46 (0.093 g, 0.141 mmol) in MeOH (2 ml) was added 1N NaOH (0.705 mmol, 0.705 ml) and stirred for 1.5 h. The solution was acidified until pH 3 with 1N HCl, then the solution was evaporated. The crude was submitted to the next reaction without further purification. -¹H NMR (200 MHz, CDCl₃) (signals were splitted for amidic isomerism): δ=1.25, 1.48 [2 s, 18H, C(CH₃)₃], 1.5–2.4 (m, 8H, CH₂—CH₂), 4.1 (m, 1H, CH₂—CH—N), 4.3 (m, 1H, N—CH—COOtBu), 5.12 (s, 2H, CH₂Ph), 6.65 (m, 1H, =CH), 7.1–7.4 (m, 5H, aromatic), 9.00 (bs, 1H, —COOH).

A solution of previous compound in xylene was refluxed for 48 h. The solvent was evaporated and the crude was purified by flash chromatography yielding 6a and 12a with a 40% of yield.

6a -¹H NMR (200 MHz, CDCl₃) (signals were splitted for amidic isomerism): δ=1.43, 1.45 [2 s, 18H, C(CH₃)₃], 1.51–2.40 (m, 10H, CH₂—CH₂), 3.75 [m, 1H, CH—N], 4.22 (m, 1H, CH—NBoc), 4.48 (t, J=17 Hz, 1H, N—CH—COOtBu), 5.7 (broad, 1H, NH).

12a -¹H NMR (200 MHz, CDCl₃) (signals were splitted for amidic isomerism): δ=1.47, 1.48 [2 s, 18H, C(CH₃)₃], 1.55–2.50 (m, 8H, CH₂—CH₂), 4.0 (m, 1H, CH—N), 4.30 (m, 1H, CH—NBoc), 4.50 (dd, J=5.4 Hz, J=17 Hz, 1H, N—CH—COOtBu), 6.0 (bd, 1H, NH).

EXAMPLE 13

Using the bicyclic lactams prepared according to the preceding examples, the respective peptidomimetics compounds, containing the RGD sequence were prepared according to the method disclosed in Gennari et al.: Eur. J. Org. Chem., 1999, 379–388.

What is claimed is:

1. A selective inhibitor of $\alpha_v\beta_3$ integrin-mediated cell attachment of the formula:

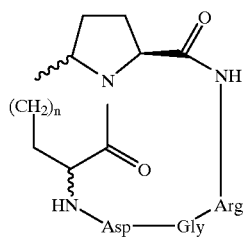

(I)

where n is 0, 1 or 2, and

Arg is the amino acid L-Arginine, Gly is the amino acid Glycine and Asp is the amino acid L-Aspartic acid or a salt thereof, or a racemate, a single enantiomer or diastereoisomer thereof.

2. A compound of claim 1 which is

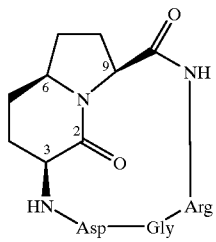

3. A compound of claim 1, which is

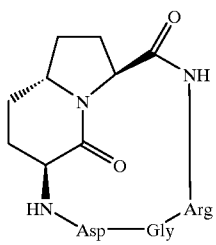

4. A compound of claim 1, which is

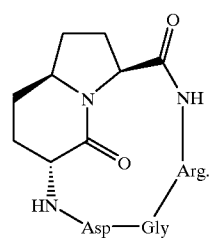

5. A compound of claim 1, which is

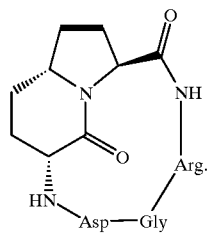

6. A compound of claim 1, which is

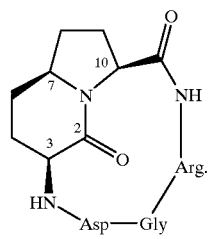

7. A compound of claim 1, which is

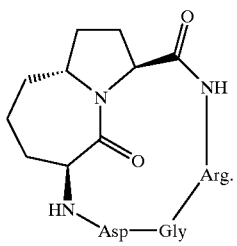

8. A compound of claim 1, which is

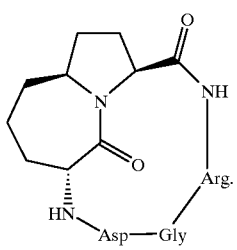

9. A compound of claim 1, which is

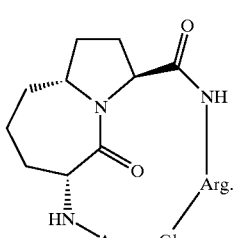

10. A method for selectively inhibiting $\alpha_v\beta_3$ integrin-mediated cell attachment to an RGD-containing ligand, comprising contacting said ligand with an effective amount of a compound of claim 1.

11. A composition comprising a compound of

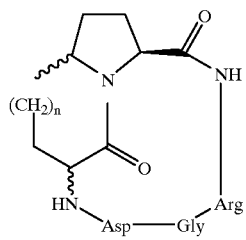

(I)

in an amount effective to inhibit $\alpha_v\beta_3$ integrin-mediated cell attachment, together with a vehicle.

12. A process for the preparation of a compound of the formula

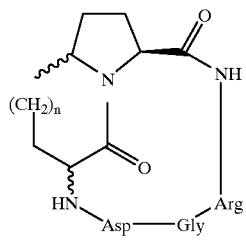

(I)

where n is 0, 1 or 2, and

Arg is the amino acid L-Arginine, Gly is the amino acid Glycine and Asp is the amino acid L-Aspartic acid or a salt thereof, or a racemate, a single enantiomer or diastereoisomer thereof, said process comprising the steps of:

a) Horner-Emmons olefination of a compound of formula (II)

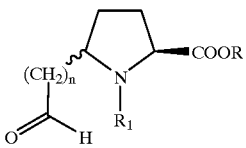

(II)

wherein R is a lower alkyl residue, and $R_1$ is a nitrogen protecting group, to give a compound of formula (III);

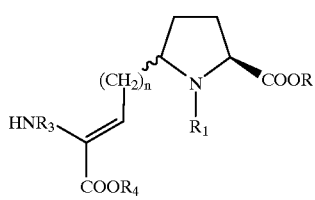

(III)

where $R_3$ is a nitrogen protecting group and $R_4$ is a lower alkyl residue;

b) hydrogenation of the compound of formula (III) and cyclization;

c) optionally, separating the stereoisomeric mixture;

d) inserting the RGD cyclic sequence; and e) optionally, separating the stereoisomeric mixture.

13. A process for the stereoselective synthesis of a compound of the formula (I)

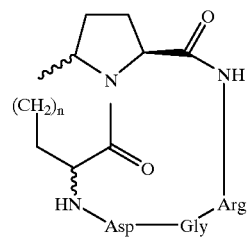

(I)

said process comprising the steps of a) Homer-Emmons olefination of a compound of formula (II)

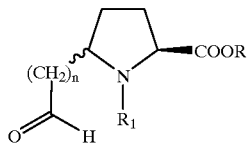

(II)

wherein R is a lower alkyl residue; and $R_1$ is a nitrogen protecting group, to give a compound of formula (III):

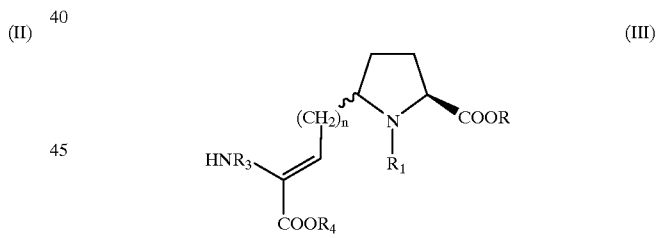

(III)

where $R_3$ is a nitrogen protecting group, $R_4$ is a lower alkyl residue;

b) hydrogenation of the compound of formula (III) by chiral phosphine-Rh catalyzed hydrogenation and cyclization;

c) optionally, separating of the stereoisomeric mixture;

d) inserting the RGD cyclic sequence; and e) optionally, separating of the stereoisomeric mixture.

* * * * *